US 8,708,491 B2

(12) United States Patent
Frey et al.

(10) Patent No.: US 8,708,491 B2
(45) Date of Patent: Apr. 29, 2014

(54) METHOD AND SYSTEM FOR MEASURING AN EYE

(71) Applicant: LensAR, Inc., Orlando, FL (US)

(72) Inventors: Rudolph W. Frey, Winter Park, FL (US); Gary P. Gray, Orlando, FL (US)

(73) Assignee: LensAR, Inc., Orlando, FL (US)

( * ) Notice: Subject to any disclaimer, the term of this patent is extended or adjusted under 35 U.S.C. 154(b) by 0 days.

(21) Appl. No.: 13/681,004

(22) Filed: Nov. 19, 2012

(65) Prior Publication Data

US 2013/0265542 A1    Oct. 10, 2013

Related U.S. Application Data

(63) Continuation of application No. 12/509,454, filed on Jul. 25, 2009, now abandoned.

(60) Provisional application No. 61/135,950, filed on Jul. 25, 2008.

(51) Int. Cl.
    *A61B 3/14*         (2006.01)

(52) U.S. Cl.
    CPC ........................................ *A61B 3/14* (2013.01)
    USPC .......................................................... 351/206

(58) Field of Classification Search
    CPC ................................... A61B 3/14; A61B 3/145
    USPC .......................................................... 351/206
    See application file for complete search history.

(56) References Cited

U.S. PATENT DOCUMENTS

| 3,074,407 | A | 1/1963 | Moon et al. |
| 3,971,382 | A | 7/1976 | Krasnov |
| 3,982,541 | A | 9/1976 | L'Esperance, Jr. |
| 4,024,852 | A | 5/1977 | L'Esperance et al. |
| 4,263,893 | A | 4/1981 | Pavlak et al. |
| 4,306,546 | A | 12/1981 | Heine et al. |
| 4,309,998 | A | 1/1982 | Aron nee Rosa et al. |
| 4,334,736 | A | 6/1982 | Herbert |
| 4,381,007 | A | 4/1983 | Doss |
| 4,394,144 | A | 7/1983 | Aoki |
| 4,403,841 | A | * 9/1983 | Lang et al. ............. 351/215 |
| 4,461,294 | A | 7/1984 | Baron |
| 4,477,159 | A | 10/1984 | Mizuno et al. |

(Continued)

FOREIGN PATENT DOCUMENTS

| EP | 0 933 060 A1 | 8/1999 |
| EP | 1 970 034 A1 | 9/2008 |

(Continued)

OTHER PUBLICATIONS

U.S. Appl. No. 11/337,127, filed Jan. 20, 2006, Frey et al.

(Continued)

*Primary Examiner* — Darryl J Collins
(74) *Attorney, Agent, or Firm* — Brinks Gilson & Lione

(57) ABSTRACT

There is provided a system, apparatus and methods for developing laser systems that can create a precise predetermined capsulotomy. The systems, apparatus and methods further provide laser systems that reduce the patient-to-patient variability and doctor-to-doctor variability associated with hand held apparatus for performing capsulorhexis and capsulotomies. There is further provided a precise predetermined shot pattern and shaped capsulotomy that is based at least in part on the shape of an IOL and in particular an accommodating IOL.

24 Claims, 20 Drawing Sheets

(56) References Cited

U.S. PATENT DOCUMENTS

| | | |
|---|---|---|
| 4,502,816 A | 3/1985 | Creter, Jr. et al. |
| 4,517,980 A | 5/1985 | Tagnon |
| 4,537,193 A | 8/1985 | Tanner |
| 4,538,608 A | 9/1985 | L'Esperance, Jr. |
| 4,554,917 A | 11/1985 | Tagnon |
| 4,561,436 A | 12/1985 | Munnerlyn |
| 4,565,197 A | 1/1986 | Daly |
| 4,573,778 A | 3/1986 | Shapiro |
| 4,576,160 A | 3/1986 | Tanaka |
| 4,579,430 A | 4/1986 | Bille |
| 4,580,559 A | 4/1986 | L'Esperance |
| 4,582,405 A | 4/1986 | Muller et al. |
| 4,583,539 A | 4/1986 | Karlin et al. |
| 4,588,505 A | 5/1986 | Walley et al. |
| 4,601,037 A | 7/1986 | McDonald |
| 4,601,288 A | 7/1986 | Myers |
| 4,607,622 A | 8/1986 | Fritch et al. |
| 4,628,416 A | 12/1986 | Dewey |
| 4,633,866 A | 1/1987 | Peyman et al. |
| 4,638,801 A | 1/1987 | Daly et al. |
| 4,644,948 A | 2/1987 | Lang et al. |
| 4,648,400 A | 3/1987 | Schneider et al. |
| 4,657,013 A | 4/1987 | Hoerenz et al. |
| 4,665,913 A | 5/1987 | L'Esperance, Jr. |
| 4,669,466 A | 6/1987 | L'Esperance, Jr. |
| 4,669,839 A | 6/1987 | Muchel |
| 4,682,595 A | 7/1987 | Hoerenz et al. |
| 4,686,979 A | 8/1987 | Gruen et al. |
| 4,686,992 A | 8/1987 | Dewey et al. |
| 4,702,245 A | 10/1987 | Schroder et al. |
| 4,702,576 A | 10/1987 | Magnante |
| 4,711,540 A | 12/1987 | Yoshino et al. |
| 4,711,541 A | 12/1987 | Yoshino et al. |
| 4,712,543 A | 12/1987 | Baron |
| 4,715,703 A | 12/1987 | Cornsweet et al. |
| 4,718,418 A | 1/1988 | L'Esperance, Jr. |
| 4,719,912 A | 1/1988 | Weinberg |
| 4,721,379 A | 1/1988 | L'Esperance |
| 4,724,522 A | 2/1988 | Belgorod |
| 4,729,372 A | 3/1988 | L'Esperance, Jr. |
| 4,729,373 A | 3/1988 | Peyman |
| 4,732,148 A | 3/1988 | L'Esperance, Jr. |
| 4,732,460 A | 3/1988 | Kele et al. |
| 4,736,744 A | 4/1988 | Koike et al. |
| 4,741,612 A | 5/1988 | Birngruber et al. |
| 4,744,362 A | 5/1988 | Gründler |
| 4,758,081 A | 7/1988 | Barnes |
| 4,765,336 A | 8/1988 | Blaha et al. |
| 4,770,162 A | 9/1988 | L'Esperance et al. |
| 4,770,172 A | 9/1988 | L'Esperance, Jr. |
| 4,770,486 A | 9/1988 | Wang et al. |
| 4,772,116 A | 9/1988 | Schroder et al. |
| 4,773,414 A | 9/1988 | L'Esperance, Jr. |
| 4,775,361 A | 10/1988 | Jacques et al. |
| 4,776,687 A | 10/1988 | Nakanishi et al. |
| 4,798,204 A | 1/1989 | L'Esperance, Jr. |
| 4,820,264 A | 4/1989 | Matsui et al. |
| 4,830,483 A | 5/1989 | Kohayakawa et al. |
| 4,832,043 A | 5/1989 | Ichihashi |
| 4,837,857 A | 6/1989 | Scheller et al. |
| 4,838,266 A | 6/1989 | Koziol et al. |
| 4,840,175 A | 6/1989 | Peyman |
| 4,846,172 A | 7/1989 | Berlin |
| 4,848,340 A | 7/1989 | Bille et al. |
| 4,854,693 A | 8/1989 | Ichihashi et al. |
| 4,856,513 A | 8/1989 | Muller |
| 4,862,888 A | 9/1989 | Yessik |
| 4,863,261 A | 9/1989 | Flammer |
| 4,865,029 A | 9/1989 | Pankratov et al. |
| 4,865,441 A | 9/1989 | Reis |
| 4,866,243 A | 9/1989 | Sakane et al. |
| 4,870,952 A | 10/1989 | Martinez |
| 4,881,808 A | 11/1989 | Bille et al. |
| 4,883,351 A | 11/1989 | Weiss |
| 4,884,884 A | 12/1989 | Reis |
| 4,887,019 A | 12/1989 | Reis et al. |
| 4,887,592 A | 12/1989 | Loertscher |
| 4,891,043 A | 1/1990 | Zeimer et al. |
| 4,900,143 A | 2/1990 | Bessler et al. |
| 4,900,145 A | 2/1990 | Akiyama |
| 4,901,718 A | 2/1990 | Bille et al. |
| 4,902,124 A | 2/1990 | Roy, Sr. et al. |
| 4,903,695 A | 2/1990 | Warner et al. |
| 4,905,711 A | 3/1990 | Bennett et al. |
| 4,907,586 A | 3/1990 | Billie et al. |
| 4,911,160 A | 3/1990 | Thyzel |
| 4,911,711 A | 3/1990 | Telfair et al. |
| 4,917,486 A | 4/1990 | Raven et al. |
| 4,931,053 A | 6/1990 | L'Esperance, Jr. |
| 4,941,093 A | 7/1990 | Marshall et al. |
| 4,951,663 A | 8/1990 | L'Esperance, Jr. |
| 4,953,969 A | 9/1990 | Fedorov |
| 4,966,577 A | 10/1990 | Crosson et al. |
| 4,972,836 A | 11/1990 | Schenck et al. |
| 4,973,330 A | 11/1990 | Azema et al. |
| 4,976,709 A | 12/1990 | Sand |
| 4,988,348 A | 1/1991 | Bille |
| 4,994,058 A | 2/1991 | Raven et al. |
| 5,000,561 A | 3/1991 | Lawniczak et al. |
| 5,000,751 A | 3/1991 | Schroder et al. |
| 5,002,571 A | 3/1991 | O'Donnell, Jr. et al. |
| 5,013,311 A | 5/1991 | Nouri |
| 5,019,074 A | 5/1991 | Muller |
| 5,041,134 A | 8/1991 | O'Donnell |
| 5,048,946 A | 9/1991 | Sklar et al. |
| 5,049,147 A | 9/1991 | Danon |
| 5,054,907 A | 10/1991 | Sklar et al. |
| 5,057,102 A | 10/1991 | Tomioka et al. |
| 5,067,951 A | 11/1991 | Greve |
| 5,090,798 A | 2/1992 | Kohayakawa |
| 5,092,863 A | 3/1992 | Schanzlin |
| 5,094,521 A | 3/1992 | Jolson et al. |
| 5,098,426 A | 3/1992 | Sklar et al. |
| 5,102,409 A | 4/1992 | Balgorod |
| 5,108,388 A | 4/1992 | Trokel |
| 5,108,412 A | 4/1992 | Krumeich et al. |
| 5,112,328 A | 5/1992 | Taboada et al. |
| 5,116,114 A | 5/1992 | Nakamura et al. |
| 5,122,135 A | 6/1992 | Durr et al. |
| 5,123,902 A | 6/1992 | Muller et al. |
| 5,128,509 A | 7/1992 | Black et al. |
| 5,133,708 A | 7/1992 | Smith |
| 5,137,530 A | 8/1992 | Sand |
| 5,141,506 A | 8/1992 | York |
| 5,147,349 A | 9/1992 | Johnson et al. |
| 5,147,352 A | 9/1992 | Azema et al. |
| 5,152,055 A | 10/1992 | L'Esperance, III et al. |
| 5,152,759 A | 10/1992 | Parel et al. |
| 5,163,934 A | 11/1992 | Munnerlyn |
| 5,171,242 A | 12/1992 | Dewey et al. |
| 5,174,021 A | 12/1992 | L'Esperance, III et al. |
| 5,178,635 A | 1/1993 | Gwon et al. |
| 5,188,631 A | 2/1993 | L'Esperance, Jr. |
| 5,194,948 A | 3/1993 | L'Esperance, III et al. |
| 5,196,006 A | 3/1993 | Klopotek et al. |
| 5,196,027 A | 3/1993 | Thompson et al. |
| 5,201,730 A | 4/1993 | Easley et al. |
| 5,202,708 A | 4/1993 | Sasaki et al. |
| 5,203,353 A | 4/1993 | Easley et al. |
| 5,207,668 A | 5/1993 | L'Esperance, Jr. |
| 5,213,092 A | 5/1993 | Uram |
| 5,215,104 A | 6/1993 | Steinert |
| 5,217,459 A | 6/1993 | Kamerling |
| 5,219,343 A | 6/1993 | L'Esperance, Jr. |
| 5,219,344 A | 6/1993 | Yoder, Jr. |
| 5,222,981 A | 6/1993 | Werblin |
| 5,224,942 A | 7/1993 | Beuchat et al. |
| 5,226,903 A | 7/1993 | Mizuno |
| 5,246,435 A | 9/1993 | Bille et al. |
| 5,246,436 A | 9/1993 | Rowe |
| 5,257,988 A | 11/1993 | L'Esperance, Jr. |
| 5,258,025 A | 11/1993 | Fedorov et al. |
| 5,263,950 A | 11/1993 | L'Esperance, Jr. |
| 5,263,951 A | 11/1993 | Spears et al. |

(56) References Cited

U.S. PATENT DOCUMENTS

| | | |
|---|---|---|
| 5,275,593 A | 1/1994 | Easley et al. |
| 5,277,911 A | 1/1994 | Viegas et al. |
| 5,279,298 A | 1/1994 | Flower |
| 5,279,611 A | 1/1994 | McDonnell et al. |
| 5,281,211 A | 1/1994 | Parel et al. |
| 5,282,798 A | 2/1994 | Bruse et al. |
| 5,284,477 A | 2/1994 | Hanna et al. |
| 5,288,293 A | 2/1994 | O'Donnell, Jr. |
| 5,290,272 A | 3/1994 | Burstein et al. |
| 5,295,989 A | 3/1994 | Nakamura |
| 5,300,020 A | 4/1994 | L'Esperance, Jr. |
| 5,300,061 A | 4/1994 | Easley et al. |
| 5,300,062 A | 4/1994 | Ueno |
| 5,300,063 A | 4/1994 | Tano et al. |
| 5,300,114 A | 4/1994 | Gwon et al. |
| 5,304,168 A | 4/1994 | Sun |
| 5,304,169 A | 4/1994 | Sand |
| 5,311,224 A | 5/1994 | Enomoto |
| 5,312,320 A | 5/1994 | L'Esperance, Jr. |
| 5,312,393 A | 5/1994 | Mastel |
| 5,314,422 A | 5/1994 | Nizzola |
| 5,318,047 A | 6/1994 | Davenport et al. |
| 5,318,560 A | 6/1994 | Blount et al. |
| 5,323,788 A | 6/1994 | Silvestrini et al. |
| 5,324,281 A | 6/1994 | Muller |
| 5,325,134 A | 6/1994 | Kohayakawa |
| 5,334,190 A | 8/1994 | Seiler |
| 5,336,215 A | 8/1994 | Hsueh et al. |
| 5,336,216 A | 8/1994 | Dewey |
| 5,342,351 A | 8/1994 | Blaha et al. |
| 5,342,370 A | 8/1994 | Simon et al. |
| 5,345,948 A | 9/1994 | O'Donnell, Jr. |
| 5,346,491 A | 9/1994 | Oertli |
| 5,347,329 A | 9/1994 | Ota |
| 5,348,551 A | 9/1994 | Spears et al. |
| 5,350,374 A | 9/1994 | Smith |
| 5,354,331 A | 10/1994 | Schachar |
| 5,355,181 A | 10/1994 | Ashizaki et al. |
| 5,356,407 A | 10/1994 | Easley et al. |
| 5,356,409 A | 10/1994 | Nizzola |
| 5,360,424 A | 11/1994 | Klopotek |
| 5,364,388 A | 11/1994 | Koziol |
| 5,364,390 A | 11/1994 | Taboada et al. |
| 5,368,590 A | 11/1994 | Itoh |
| 5,370,641 A | 12/1994 | O'Donnell, Jr. |
| 5,372,595 A | 12/1994 | Gaasterland et al. |
| 5,374,265 A | 12/1994 | Sand |
| 5,376,086 A | 12/1994 | Khoobehi et al. |
| 5,391,165 A | 2/1995 | Fountain et al. |
| 5,395,356 A | 3/1995 | King et al. |
| 5,403,307 A | 4/1995 | Zelman |
| 5,408,484 A | 4/1995 | Weimel |
| 5,411,501 A | 5/1995 | Klopotek |
| 5,412,561 A | 5/1995 | Rosenshein et al. |
| 5,413,555 A | 5/1995 | McMahan |
| 5,423,798 A | 6/1995 | Crow |
| 5,423,800 A | 6/1995 | Ren et al. |
| 5,423,801 A | 6/1995 | Marshall et al. |
| 5,425,727 A | 6/1995 | Koziol |
| 5,425,729 A | 6/1995 | Ishida et al. |
| 5,425,730 A | 6/1995 | Luloh |
| 5,437,657 A | 8/1995 | Epstein |
| 5,437,658 A | 8/1995 | Muller et al. |
| 5,439,462 A | 8/1995 | Bille et al. |
| 5,441,496 A | 8/1995 | Easley et al. |
| 5,441,511 A | 8/1995 | Hanna |
| 5,442,412 A | 8/1995 | Frey et al. |
| 5,442,487 A | 8/1995 | Mizuno |
| 5,445,633 A | 8/1995 | Nakamura et al. |
| 5,460,627 A | 10/1995 | O'Donnell, Jr. |
| 5,461,212 A | 10/1995 | Seiler et al. |
| 5,462,739 A | 10/1995 | Dan et al. |
| 5,465,737 A | 11/1995 | Schachar |
| 5,470,329 A | 11/1995 | Sumiya |
| 5,474,548 A | 12/1995 | Knopp et al. |
| 5,476,511 A | 12/1995 | Gwon et al. |
| 5,480,396 A | 1/1996 | Simon et al. |
| 5,484,432 A | 1/1996 | Sand |
| 5,489,299 A | 2/1996 | Schachar |
| 5,503,165 A | 4/1996 | Schachar |
| 5,507,740 A | 4/1996 | O'Donnell, Jr. |
| 5,514,124 A | 5/1996 | Alpins |
| 5,514,125 A | 5/1996 | Lasser et al. |
| 5,520,679 A | 5/1996 | Lin |
| 5,527,774 A | 6/1996 | Girard |
| 5,529,076 A | 6/1996 | Schachar |
| 5,531,753 A | 7/1996 | Oliveira |
| 5,533,997 A | 7/1996 | Ruiz |
| 5,548,352 A | 8/1996 | Dewey |
| 5,556,395 A | 9/1996 | Shimmick et al. |
| 5,573,544 A | 11/1996 | Simon et al. |
| 5,594,753 A | 1/1997 | Frey et al. |
| 5,607,472 A | 3/1997 | Thompson |
| 5,616,139 A | 4/1997 | Okamoto |
| 5,618,284 A | 4/1997 | Sand |
| 5,620,435 A | 4/1997 | Belkin et al. |
| 5,627,162 A | 5/1997 | Gwon et al. |
| 5,632,742 A | 5/1997 | Frey et al. |
| 5,651,782 A | 7/1997 | Simon et al. |
| 5,656,186 A | 8/1997 | Mourou et al. |
| 5,684,560 A | 11/1997 | Roffman et al. |
| 5,699,142 A | 12/1997 | Lee et al. |
| 5,709,868 A | 1/1998 | Perricone |
| 5,722,952 A | 3/1998 | Schachar |
| 5,722,970 A | 3/1998 | Colvard et al. |
| 5,731,909 A | 3/1998 | Schachar |
| 5,738,677 A | 4/1998 | Colvard et al. |
| 5,752,950 A | 5/1998 | Frey et al. |
| 5,757,462 A | 5/1998 | Nanjo |
| 5,766,171 A | 6/1998 | Silvestrini |
| 5,773,472 A | 6/1998 | Stjernschantz et al. |
| 5,828,686 A | 10/1998 | Frey et al. |
| 5,843,184 A | 12/1998 | Cionni |
| 5,849,006 A | 12/1998 | Frey et al. |
| 5,886,768 A | 3/1999 | Knopp et al. |
| 5,907,908 A | 6/1999 | Cunanan et al. |
| 5,912,915 A | 6/1999 | Reed et al. |
| 5,919,186 A | 7/1999 | Bath |
| 5,928,129 A | 7/1999 | Ruiz |
| 5,980,513 A | 11/1999 | Frey et al. |
| 5,984,916 A | 11/1999 | Lai |
| 5,993,441 A | 11/1999 | Muller et al. |
| 6,007,578 A | 12/1999 | Schachar |
| 6,013,101 A | 1/2000 | Israel |
| 6,019,472 A | 2/2000 | Koester et al. |
| 6,022,088 A | 2/2000 | Metzler |
| 6,027,494 A | 2/2000 | Frey |
| 6,055,259 A | 4/2000 | Frey et al. |
| 6,059,772 A | 5/2000 | Hsia et al. |
| 6,070,981 A | 6/2000 | Mihashi et al. |
| 6,099,522 A | 8/2000 | Knopp et al. |
| 6,114,651 A | 9/2000 | Schluter et al. |
| 6,132,424 A | 10/2000 | Tang |
| 6,186,148 B1 | 2/2001 | Okada |
| 6,190,375 B1 | 2/2001 | Frey |
| 6,197,018 B1 | 3/2001 | O'Donnell |
| 6,197,056 B1 | 3/2001 | Schachar |
| 6,252,595 B1 | 6/2001 | Birmingham et al. |
| 6,254,595 B1 | 7/2001 | Juhasz et al. |
| 6,261,220 B1 | 7/2001 | Frey et al. |
| 6,271,914 B1 | 8/2001 | Frey et al. |
| 6,271,915 B1 | 8/2001 | Frey et al. |
| 6,275,718 B1 | 8/2001 | Lempert |
| 6,280,435 B1 | 8/2001 | Odrich et al. |
| 6,280,468 B1 | 8/2001 | Schachar |
| 6,299,640 B1 | 10/2001 | Schachar |
| 6,302,879 B1 | 10/2001 | Frey et al. |
| 6,312,422 B1 | 11/2001 | Duback |
| 6,312,424 B1 | 11/2001 | Largent |
| 6,313,165 B1 | 11/2001 | Grunberger et al. |
| 6,315,773 B1 | 11/2001 | Frey et al. |
| 6,319,274 B1 | 11/2001 | Shadduck |
| 6,322,545 B1 | 11/2001 | Schachar |
| 6,322,556 B1 | 11/2001 | Gwon et al. |

(56) References Cited

U.S. PATENT DOCUMENTS

| | | |
|---|---|---|
| 6,324,191 B1 | 11/2001 | Horvath |
| 6,325,791 B1 | 12/2001 | Shimoji |
| 6,325,792 B1 | 12/2001 | Swinger et al. |
| 6,328,732 B1 | 12/2001 | Donitzky et al. |
| 6,344,040 B1 | 2/2002 | Juhasz et al. |
| 6,373,571 B1 | 4/2002 | Juhasz et al. |
| D459,806 S | 7/2002 | Webb |
| D459,807 S | 7/2002 | Webb |
| 6,413,262 B2 | 7/2002 | Saishin et al. |
| D462,442 S | 9/2002 | Webb |
| D462,443 S | 9/2002 | Webb |
| 6,451,008 B1 | 9/2002 | Frey et al. |
| 6,460,997 B1 | 10/2002 | Frey et al. |
| 6,467,906 B1 | 10/2002 | Alpins |
| 6,493,151 B2 | 12/2002 | Schachar |
| 6,494,910 B1 | 12/2002 | Ganem et al. |
| 6,497,483 B2 | 12/2002 | Frey et al. |
| 6,530,917 B1 | 3/2003 | Seiler et al. |
| 6,544,254 B1 | 4/2003 | Bath |
| 6,547,394 B2 | 4/2003 | Doherty |
| 6,554,825 B1 | 4/2003 | Murray et al. |
| 6,585,726 B2 | 7/2003 | Frey et al. |
| 6,588,902 B2 | 7/2003 | Isogai |
| 6,588,903 B2 | 7/2003 | Rathjen |
| 6,592,574 B1 | 7/2003 | Shimmick et al. |
| 6,610,686 B1 | 8/2003 | Enrico et al. |
| 6,623,476 B2 | 9/2003 | Juhasz et al. |
| 6,626,445 B2 | 9/2003 | Murphy et al. |
| 6,626,893 B2 | 9/2003 | Frey et al. |
| 6,626,894 B2 | 9/2003 | Frey et al. |
| 6,626,895 B2 | 9/2003 | Frey et al. |
| 6,626,896 B2 | 9/2003 | Frey et al. |
| 6,626,897 B2 | 9/2003 | Frey et al. |
| 6,626,898 B2 | 9/2003 | Frey et al. |
| 6,648,877 B1 | 11/2003 | Juhasz et al. |
| 6,669,342 B2 | 12/2003 | Liebermann et al. |
| 6,676,653 B2 | 1/2004 | Juhasz et al. |
| 6,693,927 B1 | 2/2004 | Horvath et al. |
| 6,726,679 B1 | 4/2004 | Dick et al. |
| 6,849,091 B1 | 2/2005 | Cumming |
| 6,863,667 B2 | 3/2005 | Webb et al. |
| 6,905,641 B2 | 6/2005 | Platt et al. |
| 6,923,955 B2 | 8/2005 | Till et al. |
| 6,962,583 B2 | 11/2005 | Kadziauskas et al. |
| 7,044,568 B2 | 5/2006 | Olivera et al. |
| 7,077,838 B2 | 7/2006 | Wong |
| 7,182,759 B2 | 2/2007 | Kadziauskas et al. |
| 7,188,949 B2 | 3/2007 | Bandhauer et al. |
| 7,220,255 B2 | 5/2007 | Lai |
| 7,252,662 B2 | 8/2007 | McArdle et al. |
| 7,264,355 B2 | 9/2007 | Rathjen |
| RE40,002 E | 1/2008 | Lin |
| RE40,184 E | 3/2008 | Lin |
| 7,338,167 B2 | 3/2008 | Zelvin et al. |
| 7,357,504 B2 | 4/2008 | Fischer et al. |
| 7,364,575 B2 | 4/2008 | Van Saarloos |
| 7,390,089 B2 | 6/2008 | Loesel et al. |
| RE40,420 E | 7/2008 | Dick et al. |
| 7,402,159 B2 | 7/2008 | Loesel et al. |
| 7,467,871 B2 | 12/2008 | Lawhorn et al. |
| 7,479,106 B2 | 1/2009 | Banik et al. |
| 7,540,613 B2 | 6/2009 | Severns |
| 7,655,002 B2 | 2/2010 | Myers |
| 7,717,908 B2 | 5/2010 | Ruiz et al. |
| 7,766,903 B2 | 8/2010 | Blumenkranz et al. |
| 7,836,894 B2 | 11/2010 | Brinkmann et al. |
| 7,959,289 B2 | 6/2011 | Cattin-Liebl |
| 8,262,553 B2 | 9/2012 | Weston et al. |
| 8,262,646 B2 | 9/2012 | Frey et al. |
| 8,382,745 B2 | 2/2013 | Naranjo-Tackman et al. |
| 8,465,478 B2 | 6/2013 | Frey et al. |
| 8,475,433 B2 | 7/2013 | Mrochen et al. |
| 8,500,723 B2 | 8/2013 | Frey et al. |
| 8,556,425 B2 | 10/2013 | Frey et al. |
| 8,617,146 B2 | 12/2013 | Naranjo-Tackman et al. |
| 2001/0029363 A1 | 10/2001 | Lin |
| 2002/0004658 A1 | 1/2002 | Munnerlyn et al. |
| 2002/0025311 A1 | 2/2002 | Till |
| 2002/0029053 A1 | 3/2002 | Gordon |
| 2002/0049437 A1 | 4/2002 | Silvestrini |
| 2002/0049450 A1 | 4/2002 | Myers |
| 2002/0103478 A1 | 8/2002 | Gwon et al. |
| 2002/0110549 A1 | 8/2002 | Till |
| 2002/0138139 A1 | 9/2002 | Till |
| 2002/0140903 A1 | 10/2002 | Schachar |
| 2002/0159028 A1 | 10/2002 | Masaki |
| 2003/0050629 A1 | 3/2003 | Kadziauskas et al. |
| 2003/0055412 A1 | 3/2003 | Lieberman et al. |
| 2003/0076477 A1 | 4/2003 | Matsumoto |
| 2003/0076508 A1* | 4/2003 | Cornsweet ............... 356/517 |
| 2003/0109926 A1 | 6/2003 | Portney |
| 2003/0135272 A1 | 7/2003 | Brady et al. |
| 2003/0139737 A1 | 7/2003 | Lin |
| 2003/0212387 A1 | 11/2003 | Kurtz et al. |
| 2003/0220630 A1 | 11/2003 | Lin et al. |
| 2003/0236515 A1 | 12/2003 | Lieberman et al. |
| 2004/0054359 A1 | 3/2004 | Ruiz et al. |
| 2004/0059321 A1 | 3/2004 | Knopp et al. |
| 2004/0070761 A1 | 4/2004 | Horvath et al. |
| 2004/0143244 A1 | 7/2004 | Gray et al. |
| 2004/0156014 A1 | 8/2004 | Piers et al. |
| 2004/0199149 A1 | 10/2004 | Myers et al. |
| 2004/0199150 A1 | 10/2004 | Lai |
| 2004/0243111 A1 | 12/2004 | Bendett et al. |
| 2004/0249403 A1 | 12/2004 | Loomas et al. |
| 2005/0107773 A1 | 5/2005 | Bergt et al. |
| 2005/0107775 A1 | 5/2005 | Huang et al. |
| 2005/0165387 A1 | 7/2005 | Lubatschowski et al. |
| 2005/0197655 A1 | 9/2005 | Telfair et al. |
| 2005/0203492 A1 | 9/2005 | Nguyen et al. |
| 2005/0241653 A1 | 11/2005 | Van Heugten et al. |
| 2005/0243276 A1 | 11/2005 | Van Heugten et al. |
| 2005/0270486 A1 | 12/2005 | Teiwes et al. |
| 2005/0286019 A1 | 12/2005 | Wiltberger et al. |
| 2006/0058682 A1 | 3/2006 | Miller et al. |
| 2006/0192921 A1 | 8/2006 | Loesel et al. |
| 2006/0195076 A1 | 8/2006 | Blumenkranz et al. |
| 2006/0215111 A1 | 9/2006 | Mihashi |
| 2006/0217688 A1 | 9/2006 | Lai |
| 2006/0259022 A1 | 11/2006 | Lin |
| 2007/0010803 A1 | 1/2007 | Bischoff et al. |
| 2007/0078447 A1 | 4/2007 | Weinacht et al. |
| 2007/0093795 A1 | 4/2007 | Melcher et al. |
| 2007/0093796 A1 | 4/2007 | Raksi et al. |
| 2007/0129693 A1 | 6/2007 | Hunter et al. |
| 2007/0173794 A1 | 7/2007 | Frey et al. |
| 2007/0173795 A1 | 7/2007 | Frey et al. |
| 2007/0185475 A1 | 8/2007 | Frey et al. |
| 2007/0265603 A1 | 11/2007 | Pinelli |
| 2008/0071254 A1 | 3/2008 | Lummis et al. |
| 2008/0111972 A1 | 5/2008 | Barth et al. |
| 2008/0186551 A1 | 8/2008 | Hanft et al. |
| 2008/0281303 A1 | 11/2008 | Culbertson et al. |
| 2008/0312675 A1 | 12/2008 | Newcott et al. |
| 2009/0069794 A1 | 3/2009 | Kurtz |
| 2009/0088734 A1 | 4/2009 | Mordaunt |
| 2009/0126870 A1 | 5/2009 | Zadoyan et al. |
| 2009/0131921 A1 | 5/2009 | Kurtz |
| 2009/0137988 A1 | 5/2009 | Kurtz |
| 2009/0137991 A1 | 5/2009 | Kurtz |
| 2009/0137993 A1 | 5/2009 | Kurtz |
| 2009/0157063 A1 | 6/2009 | Ruiz et al. |
| 2009/0161065 A1 | 6/2009 | Smith, III et al. |
| 2009/0171327 A1 | 7/2009 | Kurtz et al. |
| 2009/0177189 A1 | 7/2009 | Raksi |
| 2009/0187178 A1 | 7/2009 | Muller et al. |
| 2009/0192389 A1 | 7/2009 | Eilers et al. |
| 2009/0244482 A1 | 10/2009 | Eisener et al. |
| 2009/0281530 A1 | 11/2009 | Korn |
| 2009/0287232 A1 | 11/2009 | Davis |
| 2010/0002837 A1 | 1/2010 | Gertner et al. |
| 2010/0004641 A1 | 1/2010 | Frey et al. |
| 2010/0004643 A1 | 1/2010 | Frey et al. |
| 2010/0022994 A1 | 1/2010 | Frey et al. |

(56) References Cited

U.S. PATENT DOCUMENTS

| | | |
|---|---|---|
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0060855 A1 | 3/2010 | Graether |
| 2010/0114079 A1 | 5/2010 | Myers et al. |
| 2010/0249761 A1 | 9/2010 | Ruiz et al. |
| 2010/0256614 A1 | 10/2010 | Donitzky et al. |
| 2010/0256615 A1 | 10/2010 | Blumenkranz et al. |
| 2010/0274228 A1 | 10/2010 | Mrochen et al. |
| 2010/0292676 A1 | 11/2010 | Larsen |
| 2010/0292678 A1 | 11/2010 | Frey et al. |
| 2010/0312231 A1 | 12/2010 | Singh |
| 2010/0324542 A1 | 12/2010 | Kurtz |
| 2010/0331829 A1 | 12/2010 | Bor et al. |
| 2011/0022035 A1 | 1/2011 | Porter et al. |
| 2011/0022036 A1 | 1/2011 | Frey et al. |
| 2011/0028950 A1 | 2/2011 | Raksi et al. |
| 2011/0040293 A1 | 2/2011 | Bor |
| 2011/0092965 A1 | 4/2011 | Slatkine |
| 2011/0118712 A1 | 5/2011 | Lubatschowski et al. |
| 2011/0137301 A1 | 6/2011 | Bartoli |
| 2011/0149240 A1 | 6/2011 | Alpins |
| 2011/0160710 A1 | 6/2011 | Frey et al. |
| 2011/0160711 A1 | 6/2011 | Naranjo-Tackman et al. |
| 2011/0166557 A1 | 7/2011 | Naranjo-Tackman et al. |
| 2011/0172649 A1 | 7/2011 | Schuele et al. |
| 2011/0184395 A1 | 7/2011 | Schuele et al. |
| 2011/0187995 A1 | 8/2011 | Frey et al. |
| 2011/0190739 A1 | 8/2011 | Frey et al. |
| 2011/0190740 A1 | 8/2011 | Frey et al. |
| 2011/0292340 A1 | 12/2011 | Shimizu et al. |
| 2012/0016350 A1 | 1/2012 | Myers et al. |
| 2012/0089134 A1 | 4/2012 | Horvath et al. |
| 2012/0182522 A1 | 7/2012 | Frey et al. |
| 2012/0229767 A1 | 9/2012 | Alpins |
| 2012/0265181 A1 | 10/2012 | Frey |
| 2012/0271286 A1 | 10/2012 | Curatu et al. |
| 2012/0296321 A1 | 11/2012 | Frey et al. |
| 2012/0330290 A1 | 12/2012 | Gray et al. |

FOREIGN PATENT DOCUMENTS

| | | |
|---|---|---|
| WO | WO 03/002010 A1 | 1/2003 |
| WO | WO 2006/074469 A1 | 7/2006 |
| WO | WO 2008/112292 A1 | 9/2008 |
| WO | WO 2012/051490 A1 | 4/2012 |

OTHER PUBLICATIONS

U.S. Appl. No. 11/414,819, filed May 1, 2006, Frey et al.
U.S. Appl. No. 12/217,285, filed Jul. 2, 2008, Frey et al.
U.S. Appl. No. 12/217,295, filed Jul. 2, 2008, Frey et al.
U.S. Appl. No. 12/509,021, filed Jul. 24, 2009, Frey et al.
U.S. Appl. No. 12/509,211, Jul. 24, 2009, Frey et al.
U.S. Appl. No. 12/509,412, filed Jul. 24, 2009, Frey et al.
U.S. Appl. No. 12/685,850, filed Jan. 12, 2010, Myers et al.
U.S. Appl. No. 12/831,845, filed Jul. 7, 2010, Naranjo-Tackman et al.
U.S. Appl. No. 12/831,859, filed Jul. 7, 2010, Naranjo-Tackman et al.
U.S. Appl. No. 12/831,783, filed Jul. 7, 2010, Frey et al.
U.S. Appl. No. 12/840,818, filed Jul. 21, 2010, Porter et al.
U.S. Appl. No. 12/842,870, filed Jul. 23, 2010, Frey et al.
U.S. Appl. No. 29/377,018, filed Oct. 15, 2010, Bott et al.
U.S. Appl. No. 29/377,054, filed Oct. 15, 2010, Bott et al.
U.S. Appl. No. 13/016,593, filed Jan. 28, 2011, Frey et al.
U.S. Appl. No. 13/017,499, filed Jan. 31, 2011, Frey et al.
U.S. Appl. No. 13/017,702, filed Jan. 31, 2011, Frey et al.
U.S. Appl. No. 13/243,406, filed Sep. 23, 2011, Myers et al.
U.S. Appl. No. 13/273,653, filed Oct. 14, 2011, Frey et al.
U.S. Appl. No. 13/427,130, filed Mar. 22, 2012, Frey.
U.S. Appl. No. 13/427,149, filed Mar. 22, 2012, Frey et al.
U.S. Appl. No. 13/427,319, filed Mar. 22, 2012, Grey et al.
U.S. Appl. No. 13/435,103, filed Mar. 30, 2012, Curatu et al.
FDA PMA P030002 titled "crystalens™ Model AT-45 Accomodating Posterior Chamber Intraocular Lens (OIO)", dated Nov. 14, 2003, 16 pgs.
FDA PMA P040020 titled "AcrySof® ResSTOR® Apodized Diffractive Optic Posterior Chamber Intraocular Lenses, Models MA60d3 and SA60D3", dated Mar. 21, 2005, 29 pgs.
Bliss, E.S., "Pulse Duration Dependence of laser Damage Mechamisms", *Opto-Electronics*, vol. 3, 1971, pp. 99-108.
Chaker, M. et al., "Interaction of a 1 psec laser pulse with solid matter", *Phys. Fluids B 3*, vol. 1, Jan. 1991, pp. 167-175, plus cover page.
Chien, C. Y. et al., "Production of a high-density and high-temperature plasma with an intense high-contrast subpicosecond laser", *Optics Letters*, vol. 18, No. 18, Sep. 15, 1993, pp. 1535-1537.
Klem, D. E. et al., "The Interaction of Intense Femtosecond Laser Pulses with Solid Targets", paper prepared under the auspices of the U.S. Dept. of Energy for the Short Wavelength V: Physics with Intense Laser Pulses Second Topical Meeting on Mar. 29-31, published Dec. 30, 1992, 1993, 6 pgs.
Kuszak, J. R. et al., "Anatomy of Aged and senile Cataractous Lenses", from "Biochemistry of the Crystalline Lens", undated but prior to Jul. 2009, pp. 564-575.
Liu, X. et al., "Competition between Ponderomotive abd Thermal Forces in Short-Scale-Length Laser Plasmas", *Physical Review Letters*, vol. 69, No. 13, Sep. 28, 1992, pp. 1935-1938.
Müller, F. et al., "A Comparative Study of Deposition of Thin Films by Laser Induced PVD with Femtosecond and Nanosecond Laser Pulses", *SPIE*, vol. 1858, 1993, pp. 464-474.
Naranjo-Tackman, Ramon et al., "Subepithelial arquate (sic) incisions, using the femtosecond surgical laser, in post-phaco astigmatism: Preliminary visual and refractive results", a powerpoint presentation shown at ESCRS meeting held in London England in Sep. 2006, 8 pgs.
Sauteret, C. et al., "Laser designers eye petawatt power", *Laser Focus World*, Oct. 1990, pp. 85-92 with cover page.
Soileau, M. J. et al., "Temporal Dependence of laser-Induced Breakdown in NaCl and $SiO_2$", prepared for Dept. of Physics, North Texas State University, publication date unknown, 19 pgs.
Wilks, S. C. et al., "Absorption of ultra-Intense Laser Pulses", *Physical Review Letters*, vol. 69, No. 9, Aug. 31, 1992, pp. 1383-1386.
U.S. Appl. No. 14/142,255, Dec. 27, 2013, Naranjo-Tackman et al.
Unpublished U.S. Appl. No. 14/142,255, filed Dec. 27, 2013, 25 pgs.

\* cited by examiner

METHOD AND SYSTEM FOR MEASURING AN EYE

This application is a continuation of U.S. patent application Ser. No. 12/509,454, filed on Jul. 25, 2012 (pending), which claims the benefit of priority of provisional application Ser. No. 61/135,950 filed Jul. 25, 2008, the disclosures of each of which are incorporated herein by reference. The present invention relates to methods and systems for applying a laser to the natural human crystalline lens to address cataracts, opacifications in the lens, clear lens extraction, removal of natural lens material, use of lens replacement materials and combinations of these. The present invention further relates to methods for determining the shape and position of the natural human crystalline lens and cornea relative to a laser device so as to provide an enhanced method and system for applying a laser to the lens and cornea. The present invention additionally relates to systems and methods that provide predetermined, precise and reproducible laser shot patterns for creating a capsulotomy having a predetermined and precise shape that is reproducible from patient to patient and surgeon to surgeon.

BACKGROUND OF THE INVENTION

In general, presbyopia is the loss of accommodative amplitude. In generally, cataracts are areas of opacification of the ocular lens which are sufficient to interfere with vision. Other conditions, for which the present invention is directed, include but are not limited to the opacification of the ocular lens.

Presbyopia most often presents as a near vision deficiency, the inability to read small print, especially in dim lighting after about 40-45 years of age. Presbyopia, or the loss of accommodative amplitude with age, relates to the eyes inability to change the shape of the natural crystalline lens, which allows a person to change focus between far and near, and occurs in essentially 100% of the population. Accommodative amplitude has been shown to decline with age steadily through the fifth decade of life.

Cataracts, or the condition when the natural crystalline lens becomes opaque and clouds vision, occurs in millions of people per year and are treated effectively with surgical techniques, such as ultrasonic phacoemulsification pioneered by Kelman 30 years ago. Although the techniques have been refined over the years, safety concerns from ocular trauma, especially to the corneal endothelium from the ultrasonic energy required to break up a hardened cataract is undesirable; especially for those with a compromised corneal endothelium, such as those with Fuchs Dystrophy. Moreover, the use of lasers in the treatment of cataracts has a further issue. Cataracts scatter light, including laser light, and thus, can prevent a laser treatment beam from having the desired tissue effect. Moreover, the light scattering effect of cataracts and other opacifications can make optically determining the position and shape of the lens difficult. Accordingly, as provided in detail in this specification herein improvements in the determination of the lens position and shape, as well as, in the delivery of lasers to lens tissues including the lens capsule, cataractous and opacified tissues are provided.

The established treatment for cataracts is the removal of the opacified human crystalline lens and its replacement with an IOL. In general, IOLs consist of a small plastic lens with plastic side struts, called haptics, to hold the lens in place within the capsular bag inside the eye. Exemplary types of IOLs include monofocal lenses, multifocal IOLs which provide the patient with multiple-focused vision at far and reading distance, and accommodative IOLs which provide the patient with visual accommodation. The flexible nature of many IOLs enables them to be rolled and/or folded up for insertion into the capsule. Examples of IOL are found in U.S. Pat. Nos. 7,188,949, 6,849,091, 5,699,142 and 5,607,472, the disclosures of which are incorporated herein by reference. Commercially available IOLs that, by way of example, may benefit from the present invention are CRYSTALENS and ACRYSOF RESTOR.

A schematic representation of the shape and general structure of an example of an accommodating IOL, along the lines of a CRYSTALENS, is provided in FIG. 2. This IOL has a lens structure 202, hinges 203 located adjacent to the lens structure 202 and haptics 204, which contact the lens capsule 201. The overall shape of this IOL would be non-geometric. As used herein the term "non-geometric shape" refers to shapes other than circles and ellipses, including squares and rectangles. As used herein the term "geometric shape" refers to circles and ellipses.

The CRYSTALENS IOL was developed by Eyeonics and is presently provided by Bausch & Lomb. It is at least in part believed to be disclosed in U.S. Pat. No. 6,849,091. Further information regarding its structure and efficacy is provided by Food and Drug Administration (FDA) PMA P030002 and related documents to that PMA file. The FDA approved indicated use for CRYSTALENS was in part: "The Crystalens™ Model AT-45 Accommodating IOL is intended for primary implantation in the capsular bar of the eye for visual correction of apkakia in adult patients in whom a cataractous lens has been removed and is intended to provide near, intermediate, and distance vision without spectacles. The Crystalens™ IOL provides approximately one diopter of monocular accommodation." (Nov. 14, 2003 PMA P030002 at Part 2, Summary of Safety and Effectiveness Data, ¶ INDICATIONS FOR USE).

Thus, the CRYSTALENS is an example of an FDA approved accommodating IOL. The term "FDA approved accommodating IOL" refers to any IOL that has obtained FDA approval having an indicated use that provides for accommodation, regardless whether such IOL is actually being employed for such an approved use.

The ACRYSOF RESTOR IOL is provided by Alcon. It is at least in part believed to be disclosed in U.S. Pat. No. 5,669,142. Further information regarding its structure and efficacy is provided by FDA PMA P040020 and related documents to that PMA file. The FDA approved use for RESTOR was in part: "AcrySOF® ReSTOR® IOLs are indicated for the visual correction of aphakia secondary to removal of a cataractous lens in adult patients with and without presbyopia, who desire near, intermediate and distance vision with increased spectacle independence. The lens is intended to be placed in the capsular bag." (Apr. 24, 2004, PMA P040020, at Part 2, Summary of Safety and Effectiveness Data, ¶ INDICATIONS).

Thus, the RESTOR is an example of an FDA approved IOL for near, intermediate and distance vision. The term "FDA approved IOL for near, intermediate and distance vision" refers to any IOL that has obtained FDA approval having an indicated use that provides for near, intermediate and distance vision, regardless whether such IOL is actually being employed for such an approved use. The CRYSTALENS would also be an example of an FDA approved IOL for near, intermediate and distance vision. Moreover, the RESTOR and CRYSTALENS are examples of FDA approved IOLs that reduce and/or eliminate the need for spectacles.

The removal of the opacified natural crystalline lens and replacement with a lens replacement material, such as an FDA approved IOL, presently employs a capsulorhexis and/or a capsulotomy procedure. A capsulorhexis generally consists of the removal of a part of the anterior lens capsule and the creation of a hole or opening in the lens capsule, that results from at least in part a tearing action. A capsulotomy generally consists of a cutting of the lens capsule, without or with minimum tearing of the capsule. Thus, to remove the opacified natural lens material, the lens capsule is opened. There are several known techniques for performing a capsulorhexis and a capsulotomy.

One of these capsulorhexis techniques is a can opener approach. This approach uses a small bent needle to make small incisions around the anterior lens capsule to create an opening in the lens through which the lens could be removed. This technique quite often results in the opening in the lens capsule having ragged edges. Another of these techniques is a Continuous Curvilinear Capsulorhexis (CCC). CCC uses the same type of bent needle to begin the tear in the anterior lens capsule and then uses this needle and/or special forceps which are manually pulled to create a generally circular hole in the lens capsule. CCC, in comparison to the can opener approach, reduces the ragged edge around the opening in the lens that occurred with using the can opener technique. However CCC does not eliminate the formation of these ragged edges and there presence is dependent upon surgical skill and technique.

The use of a Fugo plasma blade to create the hole in the anterior capsule may also be used. This technique is referred to as a capsulotomy. The Fugo plasma blade is a hand held device and was originally utilized in dentistry. It is an electro magnetic device that focuses its energy on a blunt cutting filament. Information regarding the Fugo plasma blade can be found in FDA PMA K063468, K001498, K041019, and K050933.

To date is it believed that all prior techniques and apparatus and in particular all prior FDA approved apparatus for creating an opening in the anterior capsule of the lens, have to varying degrees given rise to irregular shapes, ragged edges, jagged edges, or tags in or along the edge of the opening, and/or combinations of these edge features. Moreover, it is believed that all of these prior techniques and apparatus, which are performed by hand, in general can only produce cuts or holes in the shape of a circle or an ellipse, i.e., they can only be used to provide geometric shapes and cannot be used to provide non-geometric shaped cuts. Further, because these are hand held devices the shape of these cuts varies from patient to patient and surgeon to surgeon. Thus, it is not believed that these hand held devices and non-automated techniques can provide the precise predetermined capsulotomy of the present invention.

The presence of the above described edge features, the inability to create precise predetermined and reproducible shaped cuts and the variability associated with prior techniques and apparatus for performing capsulotomies and capsulorhexises are individually and collectively undesirable and can present difficulties and problems, especially with the use of accommodative IOLs. Furthermore, the limited number of shapes for capsulotomies and capsulorhexis and the variability associated with these prior techniques is believed to be an impediment to the development of new accommodative IOLs. It is further believed that this limited number of shapes and variability is an impediment to the amount of accommodation that can be obtained from presently known IOLs and the instances where little to no accommodation is realized by the patient.

SUMMARY

It is desirable to develop systems that would reduce or eliminate these undesirable edge features, provide greater control in the creation of the opening in the lens capsule and make these improvements patient and surgeon independent, or at least, reduce the variability from patient to patient and surgeon to surgeon, associated with the formation of these undesirable features that is found with the use of present techniques and tools.

The present invention, among other things, solves this need by providing greater control in the creation of opening in the lens, in particular the creation and position of the edge of the hole, and the ability to reduce the occurrence of undesirable edge features, and do so in a manner that is less surgeon and patient dependent. Thus, there is provided herein a system and method to perform precise predetermined capsulotomies.

The novel and improved methods and systems for the performance of a capsulotomy and for measuring and determining lens position and shape, which comprise aspects of the present inventions and which are set forth in detail in the present patent specification, may provide for better implementation of other methods and systems for delivering laser beams to the lens of the eye, such as those disclosed in published applications US 2007/17379A1, US 2007/173795A1, US2007/185475A1, WO 2007/084694 A2 (now U.S. Ser. No. 12/217,295), WO 2007/084627A2 (now U.S. Ser. No. 12/217,285), the disclosures of which are incorporated herein by reference.

Provided herein are embodiments of the present invention. There is provided a system and a method of making a system for reducing eye to eye and surgeon to surgeon variability in performing procedures to create cuts in the capsule of the lens of the eye. This system comprising a therapeutic laser for producing a therapeutic laser beam, an optical path for directing the therapeutic laser beam from the therapeutic laser to the lens of the eye, and, a control system for at least directing the therapeutic laser beam in a predetermined non-geometric shaped shot pattern on a portion of the anterior capsule of the lens of the eye to create a precise predetermined non-geometric shaped capsulotomy. This system may further include a shot pattern wherein the predetermined shot pattern comprises at least one essentially straight section, wherein the predetermined shot pattern comprises at least two essentially straight sections, wherein the predetermined shot pattern comprises a first essentially straight section, a second essentially straight section, a first curved section and a second curved section, or wherein the predetermined shot pattern comprises a first essentially straight section, a second essentially straight section, a first curved section and a second curved section; and, the first essentially straight section is connected to the second and third curved sections.

There is also provided system and a method of making such system comprising a therapeutic laser for producing a therapeutic laser beam, an optical path for directing the therapeutic laser beam from the therapeutic laser to the lens of the eye, and, a control system for at least directing the therapeutic laser beam in a predetermined non-geometric shaped shot pattern on a portion of the anterior capsule of the lens of the eye to create a precise predetermined non-geometric shaped capsulotomy and having a means for determining the apex of the lens of the eye.

There is further provided a system for reducing eye to eye and surgeon to surgeon variability in performing procedures to create cuts in the capsule of the lens of the eye having a therapeutic laser for producing a therapeutic laser beam, an optical path for directing the therapeutic laser beam from the therapeutic laser to the lens of the eye, a control system for at least directing the therapeutic laser beam in a predetermined non-geometric shaped shot pattern on a portion of the anterior capsule of the lens of the eye to create a precise predetermined non-geometric shaped capsulotomy, and the shot pattern shape being based at least in part on the shape of an IOL.

There is yet further provided shot patterns for the delivery of the laser to the lens of the eye that are based upon shape of an IOL wherein the IOL is an FDA approved accommodating IOL, wherein the IOL is an FDA approved IOL for near, intermediate and distance vision, wherein the IOL is an FDA approved IOL that reduces or eliminates the need for spectacles.

There is additionally provided a system for reducing eye to eye and surgeon to surgeon variability in performing procedures to create cuts in the capsule of the lens of the eye, the system comprising, a therapeutic laser for producing a therapeutic laser beam, an optical path for directing the therapeutic laser beam from the therapeutic laser to the lens of the eye, a control system for at least directing the therapeutic laser beam in a predetermined non-geometric shaped shot pattern on a portion of the anterior capsule of the lens of the eye to create a precise predetermined non-geometric shaped capsulotomy, the shot pattern shape being based at least in part on the shape of an IOL, the IOL having at least one hinge, and the shot pattern essentially following the shape of the IOL.

There is still further provided a system for reducing eye to eye and surgeon to surgeon variability in performing procedures to create cuts in the capsule of the lens of the eye, comprising a control system for at least directing the therapeutic laser beam in a shot pattern on a portion of the anterior capsule of the lens of the eye to create a cut in the capsule, the shot pattern having an X, Y and Z direction component, the delivery of the shots in the shot pattern relative to the X, Y and Z directional components being delivered in a jigsaw cut, having a Z direction sweep, and wherein the Z direction sweep is of a magnitude that it substantially reduces the number of missed cuts which reduces eye to eye and surgeon to surgeon variability.

There is also provided a method for making a laser device for creating a precise predetermined capsulotomy, said method comprising obtaining a laser device having a therapeutic laser, analyzing an IOL to obtain information about the IOL, developing a non-geometric shaped shot pattern for the delivery of the therapeutic laser to the capsule of the lens of the eye, said development being based at least in part upon the information obtained from said analysis, and, providing the non-geometric shot pattern to said laser device. By way of example such providing can be accomplished by supply or downloading a program to the laser controller containing the information regarding the shot pattern.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

DESCRIPTION OF THE DRAWINGS AND THE PREFERRED EMBODIMENTS

In general, the present inventions relates to methods and systems for providing a laser to the natural human crystalline lens to address cataracts, opacifications in the lens, clear lens extraction, removal of natural lens material, replacement of that material with replacement material, and combinations of these. The present invention further relates to methods for determining the shape and position of the lens so as to provide an enhanced method and system for providing a laser to the natural human crystalline lens for addressing these conditions.

Figure 1:
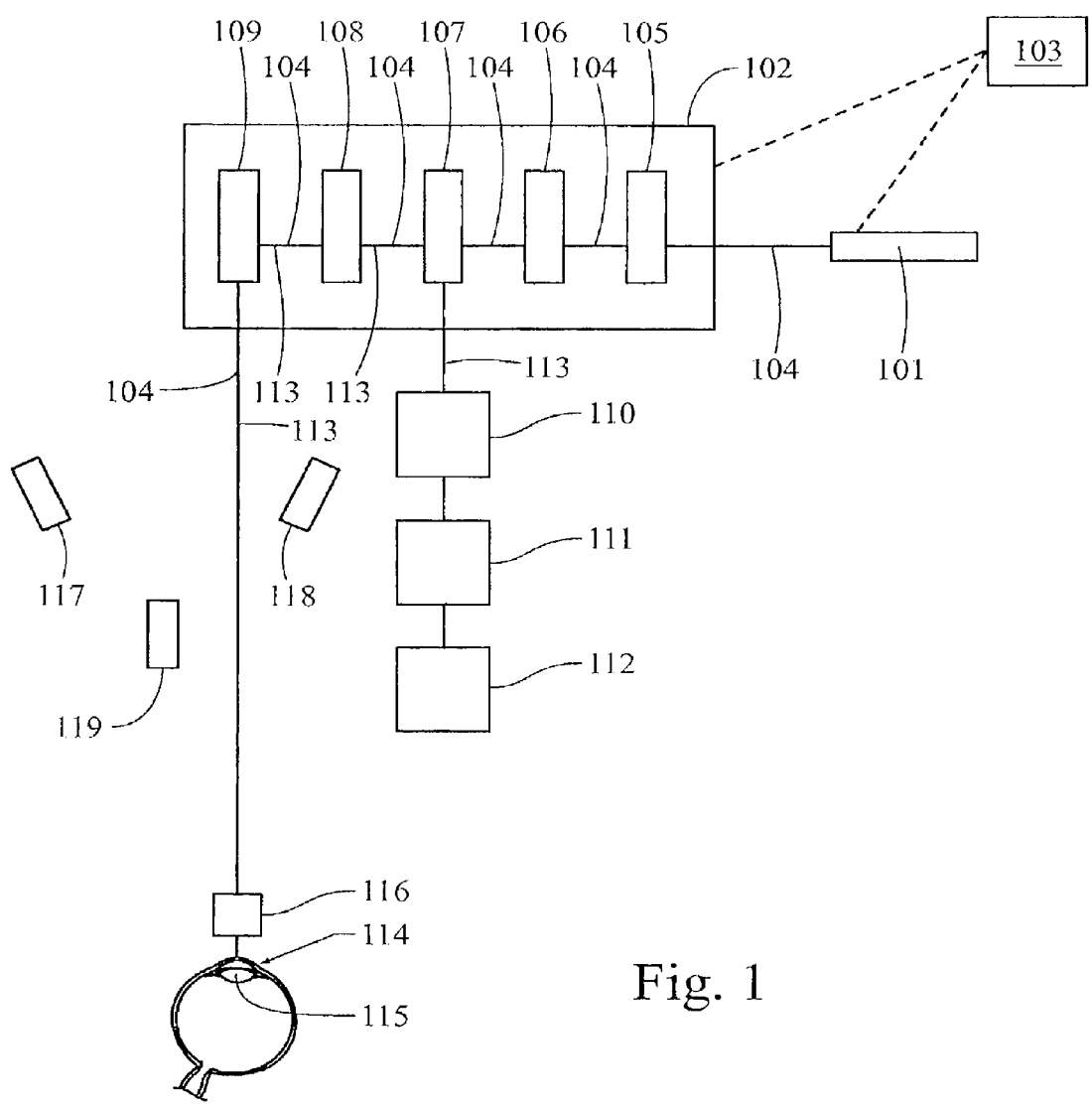
FIG. 1 is a schematic diagram of a type of system for delivering a laser beam shot pattern to the lens of an eye.

The present invention provides a system and method for determining the location, shape and apex of the lens and cornea with respect to the laser device or system and for the use of this determination in performing a capsulotomy and in performing the removal of the clear, opacified, or cataractous lens material of a natural crystalline lens. Thus, in general a laser system, i.e., a laser device, for treating patients is provided as shown by way of example in FIG. 1. In this system there is provided a treatment laser 101; optics for delivering the laser beam 102; a control system for delivering the laser beam to the lens in a particular pattern 103, which control system 103 is associated with and/or interfaces with the other components of the system, as shown for example by dashed lines in FIG. 1, and/or other control systems not shown in FIG. 1.

In general, the treatment laser 101 should provide a beam 104 that is of a wavelength that transmits through the cornea, aqueous and lens. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser. In particular, wavelengths of about 300 to 2000 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers are disclosed in 2007/084694 A2 and WO 2007/084627 A2, which are incorporated herein by reference. These and other similar lasers may be used a therapeutic lasers.

In general, the optics for delivering 102 the laser beam 104 to the natural lens of the eye should be capable of providing a series of shots to the natural lens in a precise and predetermined pattern in the x, y and z dimension. The optics should also provide a predetermined beam spot size to cause photodisruption by the laser pulses delivered to the lens or cornea.

In general, the control system 103 for delivering the laser beam 104 may be any computer, controller, and/or software hardware combination that is capable of selecting and controlling x y z scanning parameters and laser firing. These components may typically be associated at least in part with circuit boards that interface to the x y scanner, the z focusing device and/or the laser. The control system may also, but does not necessarily, have the further capabilities of controlling the other components of the system, as well as, maintaining data, obtaining data and performing calculations. Thus, the control system may contain the programs that direct the laser through one or more laser shot patterns. Similarly, the control system may be capable of processing data from the slit scanned laser 117 and camera 118 and/or from a separate controller for the slit scanned laser system or camera.

The laser optics for delivering 102 the laser beam 104 comprise a beam expander telescope 105, a z focus mechanism 106, a beam combiner 107, an x y scanner 108, and focusing optics 109. There is further provided relay optics 110, camera optics 111, which include a zoom, and a first ccd camera 112.

Optical images 113 of the eye 114 and in particular optical images of the natural lens 115 of the eye 114 are conveyed along a path 113. This path 113 follows the same path as the laser beam 104 from the natural lens 115 through the laser patient interface 116, the focusing optics 109, the x y scanner 108 and the beam combiner 107. There is further provided a laser patient interface 116, and a structured light source 117 and a structured light camera 118, including a lens.

A structured light source 117 may be a slit illumination having focusing and structured light projection optics, such as a Schafter+Kirchhoff Laser Macro Line Generator Model 13LTM+90CM, (Type 13LTM-250S-41+90CM-M60-780-5-Y03-C-6) or a StockerYale Model SNF-501L-660-20-5, which is also referred to as a slit scanned laser. In this embodiment the structured illumination source 117 also includes slit scanning means 119.

When using a scanned slit illumination the operation includes positioning the slit at an acute angle to the crystalloine lens' AP axis and to one side of the lens, taking an image then maintaining the same angle, moving the slit a predetermined distance, then taking another image, and then repeating this sequence until the entire lens is observed through the series of slit sections. The nominal slit angle can be approximately 15 to 30 degrees from the AP axis. Any visible or near IR wavelength source compatible with the camera may be used. Low coherence length sources are preferable to reduce speckle noise.

The structured light illumination source 117 and the structured light camera 118 are arranged in an angled relationship. The angled relationship may be but is not required to be in the so-called Scheimpflug configuration, which is well-known. The structured light source 117, in conjunction with the slit scanning means 119, projects a line and or a plurality of lines onto the eye lens 115 at an angle or plurality of angles. The light scattered at the eye lens 115 forms the object to be imaged by the lens 247 and focused onto the camera system 118. Since the slit illuminated image in the eye lens 115 may be at a large angle with respect to the camera 118, this presents a large depth of field to the camera and the entire slit image may not be in sharp focus at the camera. By tilting the camera at an angle or plurality of angles the image along the illuminated plane can be in sharper focus. To the extent that a shaper focus is not obtained, arithmetic data evaluation means are further provided herein to determine a more precise location of the illuminated structures with respect to the laser device.

The images from the camera 118 may be conveyed to the controller 103 for processing and further use in the operation of the system. They may also be sent to a separate processor and/or controller, which in turn communicates with the controller 103. The structured light source 117, the camera 118 and the slit scanning means 119 comprise a means for determining the position, shape and apex of the lens and cornea in relation to the laser system. Alternate means of measuring the position, shape and apex of the lens and cornea may be used in lieu of the specific embodiment described herein. Other equivalent biometric methods for measuring the lens and cornea include rotating Scheimpflug configurations such are used in the commercial PENTACAM OCULUS device, optical coherence tomography (OCT) and B-scan ultrasound technologies.

In general, the present invention provides for the delivery of the laser beam in patterns that utilize, or are based at least in part on, lens geometry, curvature of the lens and/or the position and location of the lens and cornea with respect to various apparatus. More specifically, the invention could utilize measurements of the radii or curvature, center of curvature and apex of the lens and cornea to control the position and orientation of the capsulotomy and the position and shape of the envelope of cuts in the lens nucleus used to fragment the lens for removal. As part of the present invention the concept of matching and/or compensating for the curvature and position of the capsule of the lens is provided. Anterior and posterior lens curvatures and lens location measurements can be used in the context of Kuszak aged lens models, Burd's eye model, Burd et al. Vision Research 42 (2002) 2235-2251, or on specific lens measurements to determine the position of the capsulotomy and shape of the envelope defining the boundary of cuts within the lens fibrous mass. Thus, in general, these laser delivery patterns are based in whole and/or in part on the mathematical modeling and actual observation data regarding the shape of the lens, the position of the lens and/or the geometry of the lens.

The delivery of laser shot patterns for the removal of lens material is provided. Three primary activities are provided herein. The first activity involves the anterior surface of the lens capsule. The second activity involves the lens material that is contained within the capsule, i.e., the interior structures of the lens, such as the cortex and the nucleus and cataractous material contained therein. The third activity involves the use of a lens replacement material, including but not limited to IOLs, within the lens capsule after interior structures of the lens have been removed.

Thus, there are provided novel methods and systems for producing cuts, i.e., incisions in the anterior lens capsule. These cuts are created by the therapeutic laser beam 104 being delivered to the anterior lens capsule in precise predetermined and highly reproducible patterns, delivery results in precise predetermined and highly reproducible shaped cuts in patterns as described and taught herein, or as may be called for by the use of a particular IOL or other device or material to be inserted within the lens capsule. As used herein geometric shaped patterns or cuts refers to circular and elliptical shaped patterns or cuts. As used herein non-geometric shaped patterns or cuts refers to all other shapes that are not circular or elliptical.

The methods and systems to create these cuts in the anterior capsule provide superior results to the handheld methods and apparatus previously known for performing capsulorhexus and capsulotomy, and thus, the methods and systems disclosed herein are considered to be a substantial advancement in these techniques.

In addition the delivery of the laser beam shots in a manner that greatly reduces the risk of a missed cut, which depending upon the particular application may be very significant is provided. Moreover, as provided in the following examples, anterior capsule cuts are envisioned and provided that may be a continuous cuts, cuts and lands (uncut capsule portions between cuts) and perforations. Thus, as used herein the terms "missed cut" or "missed cuts" refer to a cut that was intended to be carried out by the delivery of a particular laser shot pattern, but which did not occur because the laser beam missed the lens capsule or targeted lens material. Thus, in a cut and land pattern the lands would not be considered missed cuts, if they were intended to be left uncut by the laser pattern.

The cuts in the lens anterior surface are for the purpose of creating an opening in the lens capsule for the removal of the interior structures of the lens. To facilitate this removal there are provided various laser shot patterns that cut the interior structure of the lens into small volumes, which volumes can then be removed from the lens capsule. These small volumes can range from about 0.064 $mm^3$ to about 8 $mm^3$. Thus a grid laser shot pattern within the interior structures of the lens, which creates cube shaped volumes of interior lens material, can be employed. These cubes can range in size from a side having a length of about 0.4 mm to about 2 mm with the characteristic dimension of the cube chosen in part to match the internal diameter of the tip of aspiration probe to be used to remove the lens tissue. Additionally, this invention is not limited to the formation of cubes and other volumetric shapes of similar general size may be employed. For example arrangement of other shapes such as triangles and pie sliced volumes may be employed.

The laser cut in the anterior capsule is used to create a small opening in the lens anterior surface of the lens capsule for removal of the sectioned volumes of interior material. Thus, this procedure may be used to treat cataracts. This procedure may also be used to remove a lens having opacification that has not progressed to the point of being cataractous. This procedure may further be used to remove a natural lens that is clear, but which has lost its ability to accommodate. In all of the above scenarios, it being understood that upon removal of the lens material the lens capsule would subsequently house a suitable replacement, such as an IOL, accommodative IOL, or synthetic lens refilling materials. Moreover, the size and the shape of the opening is variable and precisely controlled and preferably for presently known lens refilling materials and IOLs is 2 mm or less diameter for lens refilling applications and about 5 mm for IOLs.

The order in which these activities are performed may depend upon the particular characteristics of the internal lens structure, the density of the cataract, the position of the cataract, the type of device used to remove the internal lens material once it has been sectioned into small volumes, the type and power of the laser used, the amount and size of gas bubbles that are produced by the laser, and other factors. Thus, although the examples herein provide for an order of performing the activity of cutting the anterior surface of the lens and sectioning the interior structures of the lens, it should be recognized that this order can be changed, as well as performed essentially simultaneously.

The laser system for treating patients of the present invention is capable of making precise and predetermined cuts in the capsule of the lens thus giving rise to capsulotomies that are of precise and predetermined shapes. Thus, there is provided the method of obtaining and analyzing the shape and structure of an IOL, and in particular obtaining and analyzing the shape and structure of an accommodating IOL, an IOL that reduces and/or eliminates the need for spectacles, and/or an IOL for near, intermediate and distance vision, including but limited to FDA approved versions of said IOLs. Based upon this analysis an optimized shape and position for the capsulotomy for use with a particular IOL, or grouping of similarly shaped IOLs, is determined. A predetermined shot pattern for making this optimized shaped capsulotomy is then provided to the laser system, preferably by providing the shot pattern to the control system 103. The laser system can then be used for one or all of the following procedures, determining the shape and position of the anterior surface of the lens, and in particular the anterior surface of the lens capsule, determining the apex of the lens capsule in relation to the laser system, performing a laser capsulotomy having the precise and predetermined shape selected for a particular type of IOL, and removal of the natural lens material.

Figure 3:
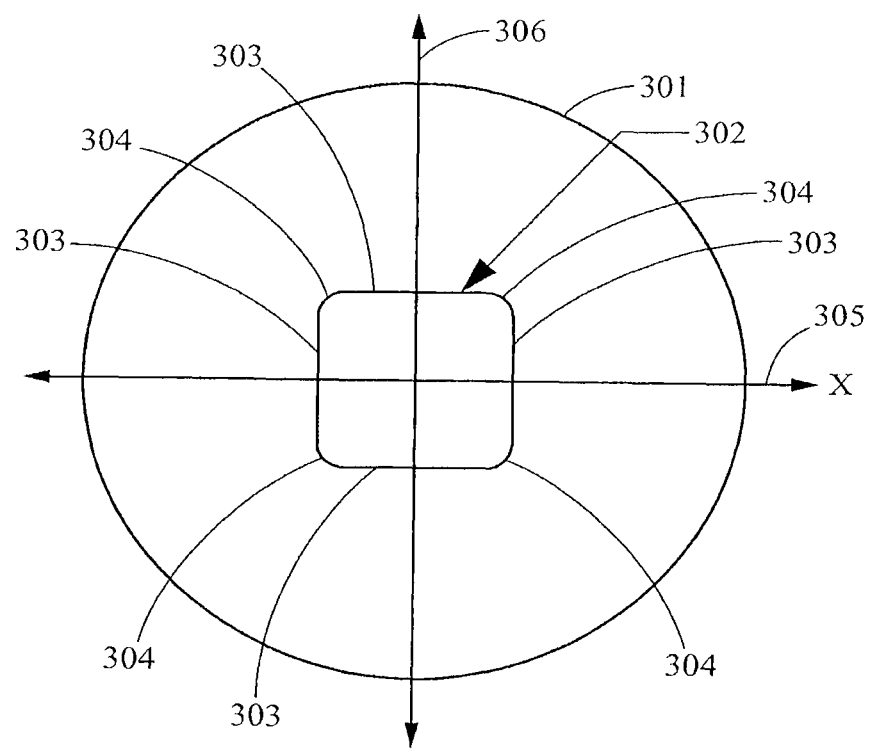
FIGS. 3 and 4 are diagrams of shot patterns.

Thus, for example, the shape of a precise capsulotomy and its corresponding shot pattern may consist of essentially straight sides, which each side being connected by curved or rounded sections. An example of this type of predetermined cut is illustrated in FIG. 3. Thus, there is provided in FIG. 3 a lens capsule 301, which x and y axis 305 and 306 respectively, shown in this figure for reference purposes. There is further illustrated a predetermined shot pattern 302 having essentially straight sections 303, which are connected by curved sections 304. The shot pattern of FIG. 3 would be an example of a non-geometric shaped pattern as that term is used herein. This shot pattern when implemented by the laser system provides a precise predetermined cut in the lens capsule, a precise predetermined opening in the lens capsule and a precise predetermined capsulotomy of the shape illustrated in this figure. The essentially straight sections of the predetermined shot pattern may be from about 0.25 mm to about 4.5 mm. As used herein, and section of an opening, capsulotomy, cut or shot pattern that is essentially straight for a length of more that 0.2 mm is considered to be an essentially straight section of a cut or pattern.

Figure 4:
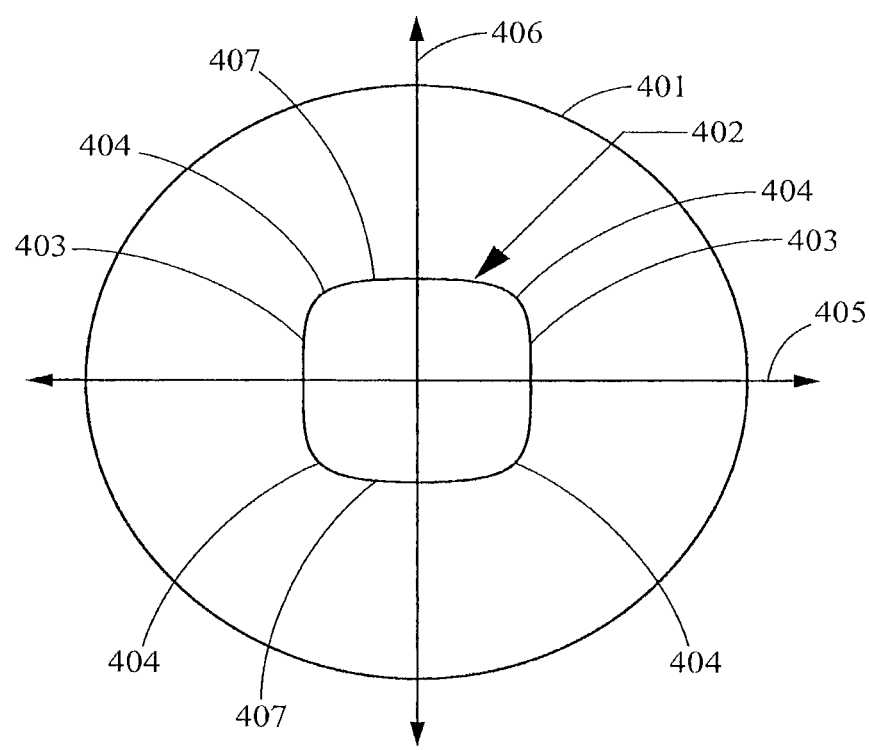

The precise and predetermined shot pattern, opening, capsulotomy and cut may have only a single straight section or it may have two, three, four, five, or more. Moreover, in addition to essentially straight sections, there may be sections in which the radius of curvature is substantially reduced in comparison to other sections of the pattern, opening, capsulotomy or cut. Thus, for example, as shown in FIG. 4 there is provided a lens capsule 401, which x and y axis 405 and 406 respectively, shown in this figure for reference purposes. There is further illustrated a predetermined shot pattern 402, which when implemented by the laser system will create a precise predetermined cut, i.e., capsulotomy, having two essentially straight sections 403, four curved sections 404 and two section having a substantially increased radius of curvature 407. Accordingly, each essentially straight section 403 is connected to a substantially increased radius of curvature section 407 by a curved section 404.

Figure 2:
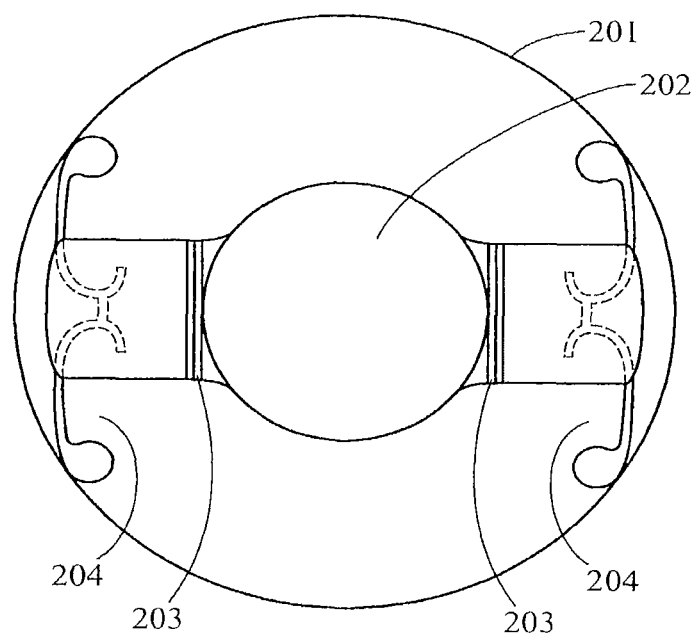
FIG. 2 is a diagram of an accommodating IOL.
Figure 5:
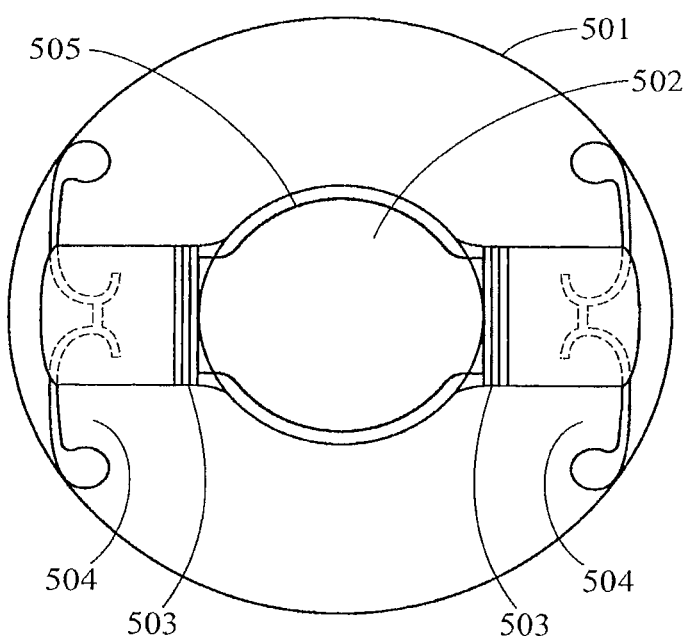
FIG. 5 is a diagram showing the shot pattern of FIG. 4 positioned on the lens of the eye in relation to the accommodating IOL of FIG. 2.

FIG. 5 illustrates a precise predetermine non-geometric cut that can be created by implementing the predetermined shot pattern in relation to the type of IOL shown in FIG. 2. Thus, there is provided an IOL lens structure 502, hinges 503 located adjacent to the lens structure 502, and haptics 504, which contact the lens capsule 501. There is further provided a precise predetermined non-geometric capsulotomy 505, having two curved section and two essentially straight sections. The positioning of these sections is further illustrated in FIG. 5, with the essentially straight sections being positioned inside of the hinges, i.e., toward the lens structure. This cut and pattern would be an example of a cut, opening, capsulotomy and pattern that essentially follow the shape of an IOL. This type of cut has been referred to as an ALL-ON cut, i.e., the cut is on or over all of the IOL.

Figure 6:
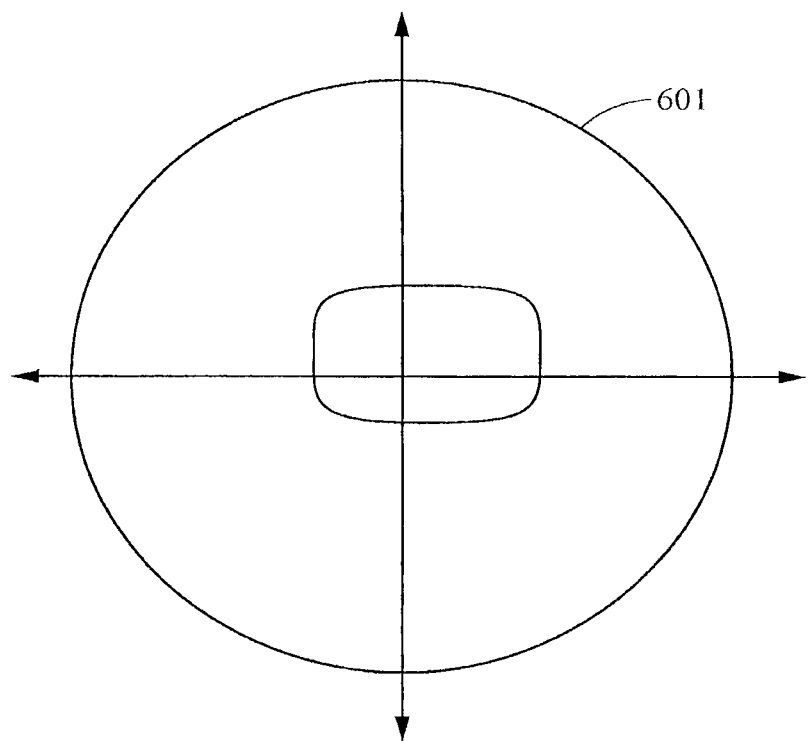
FIG. 6 is a diagram of a shot pattern.

FIG. 6 is an illustrative example showing that the pattern and cut can be move off center with respect to the capsule 601.

Thus, there is provided techniques, systems and apparatus to deliver laser beam in a shot pattern to the lens of the eye and in particular to the capsule of the lens of the eye in a precise and predetermined manner to provided for a precise predetermined capsulotomy. The shape of these patterns may be delivered using either the jigsaw or ring delivery sequences provided herein.

When performing laser assisted cataract surgery the process of cutting the nucleus with a photodisruption laser can cause a buildup of gas bubbles sufficiently near the soft cortex to allow the gas bubbles to propagate toward the capsule. In those situations where bubbles collect in close proximity to the anterior capsule, when the laser attempts to cut the capsulotomy, the sudden release of bubbles may change the position of the anterior capsule during the delivery of the laser shot pattern causing the laser to miss the capsule resulting in missed cuts, at least partially around the circumference of the capsulotomy. To solve this problem, there is provided herein a special cutting pattern that is less dependent of capsule position versus time and provides cutting of the capsule despite position changes of the capsule during the laser capsulotomy procedure. Thus, resulting in substantially reduced or no missed cuts.

There is provided herein the use of laser shot patterns having a large range of Z swept at a high rate of speed, while the XY position is moved in a circular, or elliptical or other pattern or desired shape, more slowly so that the laser cutting action occurs multiple times over essentially the same XY position. Thus, it could be envisioned that the laser beam is operating like the tip of a jigsaw blade moving up and down rapidly compared to the XY positioning to create the cut shape. In this way, if the anterior capsule shifts during the cut, due to gas bubble propagation or any other reason, the cut will still be made to the capsule, albeit perhaps outside the center region of the z direction up-down distribution of shots, and more to the anterior or posterior ends of that distribution. For laser cutting of the nucleus where a great deal of bubble buildup is created, a Z range, or up-down range of the cut should be approximately 1 mm in extent, nominally centered on the anterior capsule which would allow approximately +/−475 µm of capsule movement and still provide cutting of a 25 µm thick capsule.

In addition to enabling cutting of a capsule that moves move during the procedure, this procedure can be used to compensate for static errors in capsule position due to for example measurement errors. In this way the extent of the Z range may be increased by the known error of the system.

In addition to the large Z range sweeps disclosed herein, there is also contemplated the use of a smaller Z range of cut motion for the case where the uncertainty in capsule position from both static measurement error and anticipated change in position might be smaller, perhaps in the range of hundreds of µm or in the case of highly precise measurement data and near zero movement of the capsule during surgery. In such a case the Z range could be tens of µm—enough range to cut through the capsule thickness.

The Z range sweep in the capsulotomy shot pattern provides for the ability to optimize laser surgery efficiency in cataract removal procedures. Thus, the nucleus of the lens can be sectioned into small volumes before the capsulotomy is performed. In this way any gas bubbles that are formed by the sectioning of the nucleus will be trapped within the capsule. By keeping the gas bubbles inside of the capsule, their effect on laser delivery is reduced, when compared to their effect if they escape from the capsule and migrate into the aqueous or collect and build up next to the posterior of the cornea. The detrimental effect of shooting the laser beam through a bubble increases as the distance that the beam has to travel after passing through the bubble before reaching its intended point increases. Thus, by trapping the bubble in the capsule this distance is keep to an absolute minimum and thus the detrimental effect of shooting through the bubbles is similarly minimized.

The accumulation of bubbles within the capsule, however, increases the likelihood that the lens and/or capsule will shift during the capsulotomy as the bubbles escape through the cuts in the lens capsule. As noted above this shifting could result in missed cuts and an incomplete capsulotomy. Thus, the Z range sweep avoids any missed cuts from lens or capsule movement and accordingly provides the synergistic advantages of increased laser efficiency, reduced detrimental effect of gas bubbles, and reduced missed cuts in the capsulotomy.

Thus there is provided a system and method to optimize laser surgery efficiency in an embodiment of the invention by allowing the nucleus to be cut first, and the gas bubbles formed from such cutting contained within the capsule, until the capsulotomy is performed. The containing of the gas bubbles within the capsule avoids having to shoot through bubbles in the anterior chamber caused but creating the capsulotomy first. This solution, however, can lead to the accumulation of bubbles inside the fibrous mass of the lens which may cause the capsule to move during capsulotomy. To address this potential movement the invention further provides for the varying z direction movement of the laser beam. However, it is also understood that, one case where the uncertainty of capsule movement is small is the case where the capsulotomy is laser cut prior to the cutting of the nucleus material and no bubbles have been placed in the lens. In this case if the uncertainty in position is sufficiently small that the extent of the z range is sufficiently small, that only a superficial amount of bubbles may be present in the anterior chamber which may not interfere with laser cutting of the nucleus. It should further be understood that when referring to a sequence of cutting structures, such as described in this paragraph, that a step the order of sequence is defined by when a substantial majority of the cuts are performed in the one structure before another structure, i.e., the placement of a few laser shots in an other structures during delivery of the shot pattern to the first structure will not prevent the first structure from being considered the first structure in the sequence.

A further embodiment of the present systems and methods is to define a high accuracy position measurement of the anterior capsule, so as to provide in general greater accuracy, precisions and reproducibility from patient to patient for the capsulotomy. Thus, there is provided a method applying slit technology with new and innovative methods to determine the apex of the lens of the eye, with respect to the therapeutic laser device, and thus, providing accurate measurements and relative position determinations for performing procedures on the lens of the eye.

Figure 13:
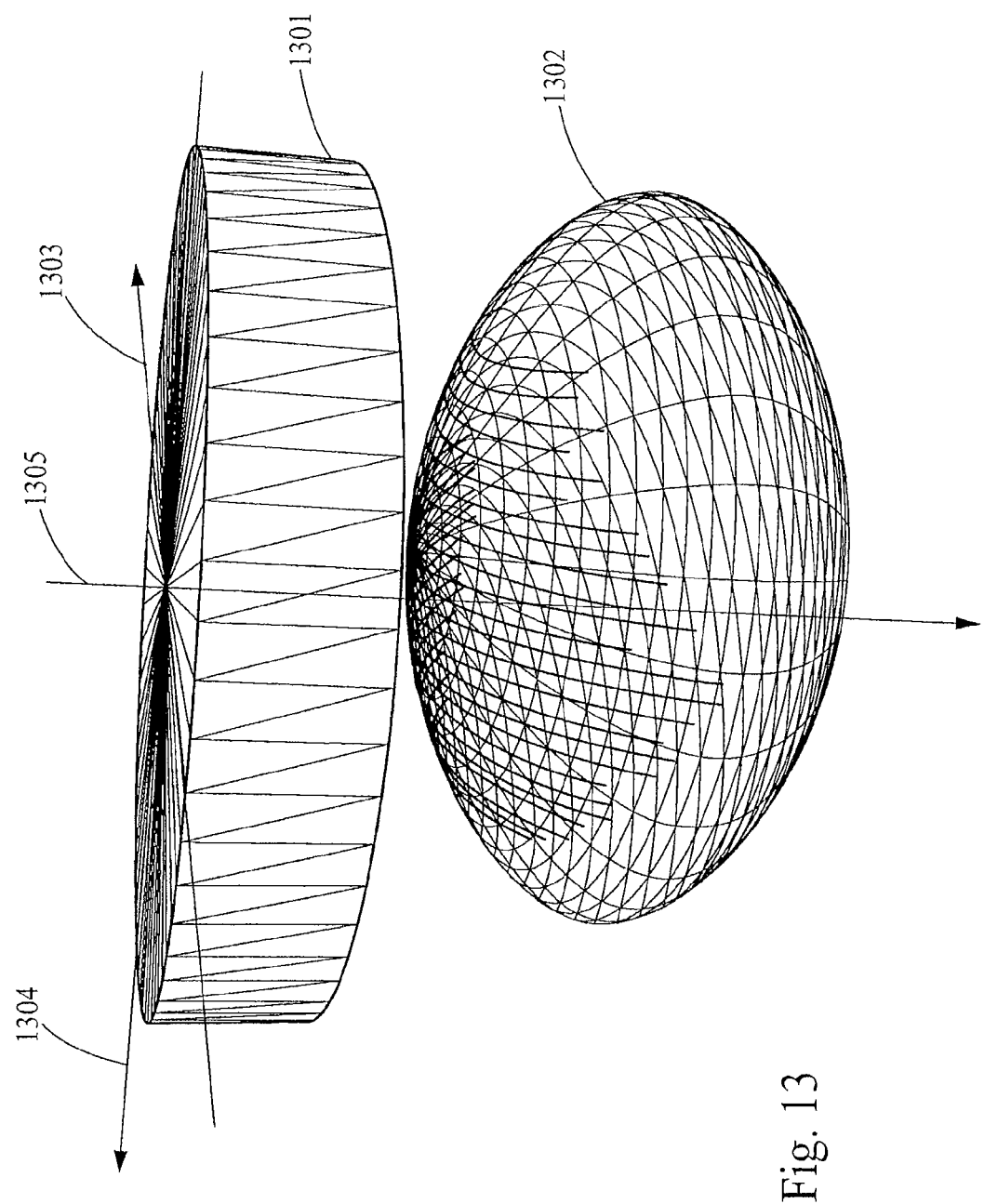
FIGS. 13-20 are diagrams illustrating the paths of slit scanned light with respect to the lens of the eye.

Thus, turning to FIGS. 13-19 there is provided a series of drawings showing the use of the laser structured light source 117 projection onto the lens of a human eye through a glass plate. FIG. 13 shows the general configuration of the glass plate and lens. FIGS. 14-19 show the path of the light from the slit lamp to the glass plate and the lens and the return paths of light beams from the glass plate and the lens, as the location of the slit lamp's impingement on the glass plate and the lens is changed. Like components in FIGS. 13-19 have like numbers, thus, for example glass plate 1301, 1401, 1501, 1601 and 1701 are the same In FIG. 13 there is provided a glass plate 1301 positioned in relation to a human lens 1302 having an X axis 1303, a Y axis 1304 and a Z axis 1305. The glass plate 1301 has a thickness of 1.57 mm and an index of refraction of 1.57.

Figure 14:
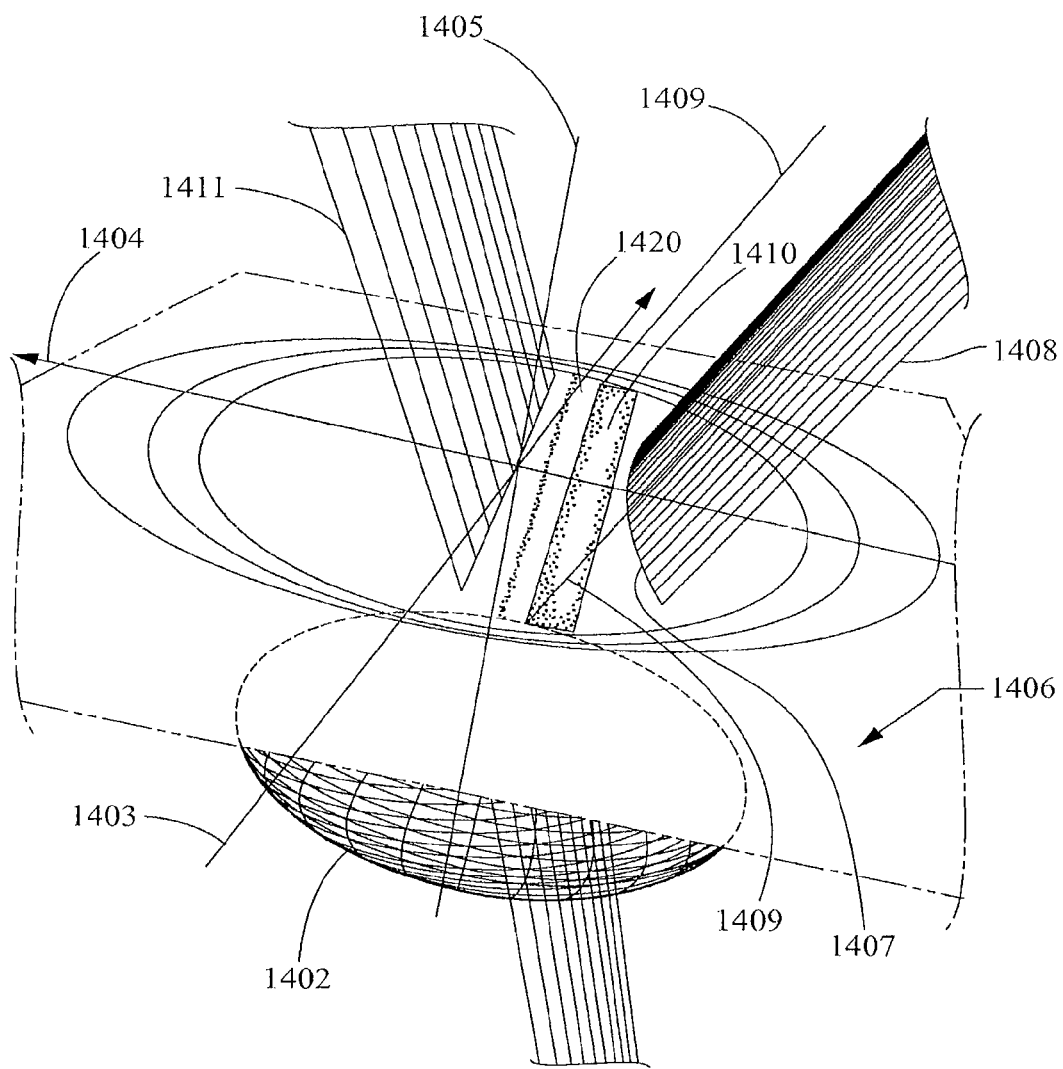
Figure 15:
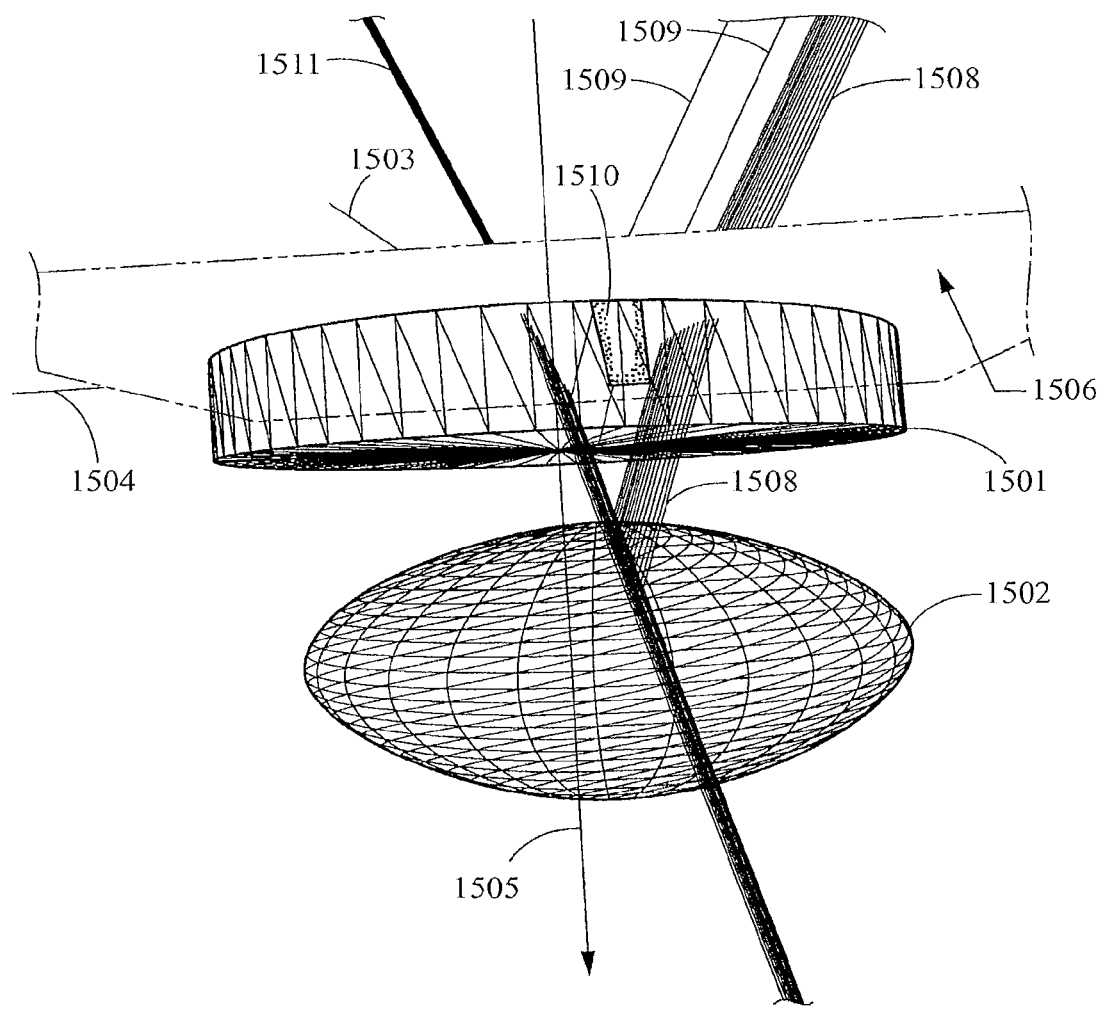

In FIG. 14 is a top view of the glass plate (not seen) and lens 1402 of FIG. 13. In FIG. 14 there is provided an X axis 1403, a Y axis 1404, an XY plane 1406 and a Z axis 1405. In this figure light beams 1411 from a slit lamp are directed through the XY plane 1406 to the glass plate and lens 1402. The light travels back from the glass plate and lens 1402, providing an image of the glass plate 1420 and applanated cornea 1410, beams of light 1409 from the bottom of the glass plate (by bottom is it meant the side of the glass plate closest to the lens), beams of light 1408 from the anterior surface of the lens 1402, and a line 1407 based upon the beams 1408, which represents the curvature of the lens 1402 at the point where the light 1411 illuminates it. FIG. 15 is a view of the same system and light paths but from below the XY plane 1506. (Again like numbers correspond to like components, thus beam 1508 is the same as beam 1408).

Figure 16:
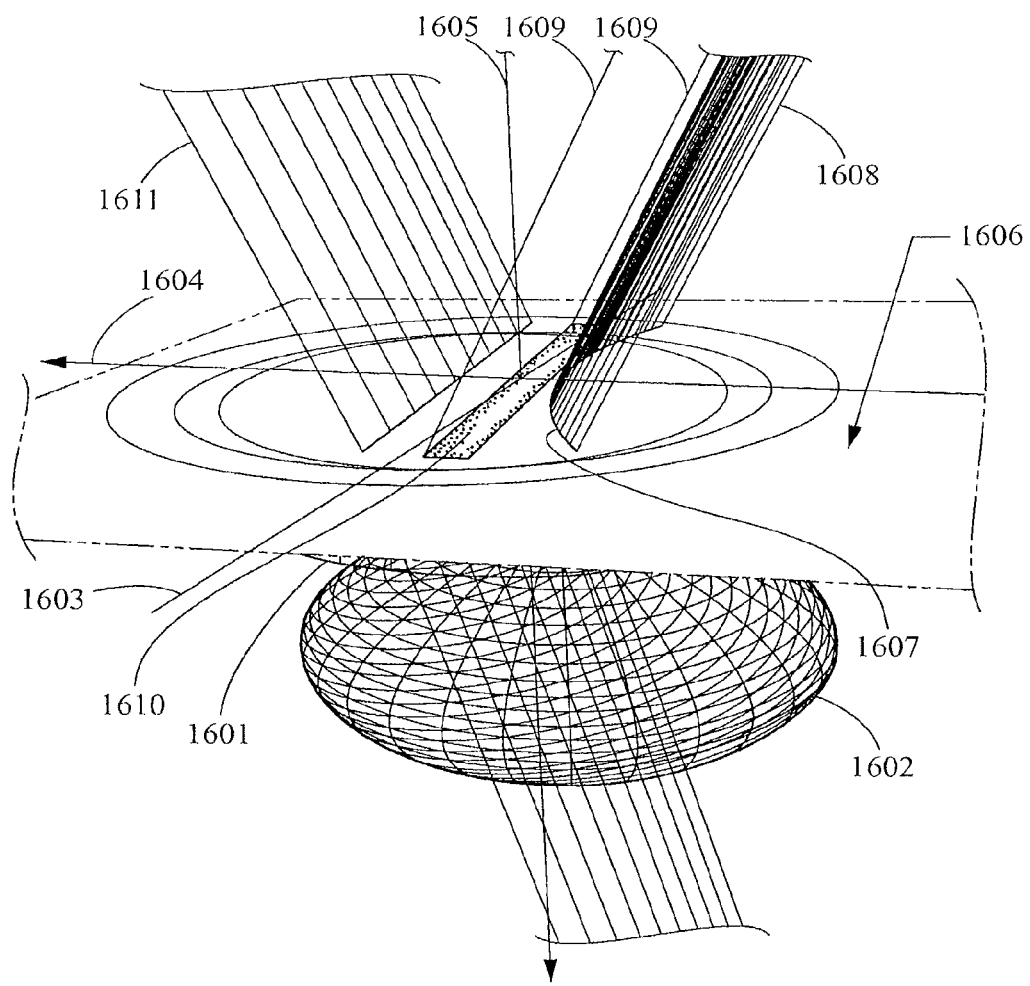

FIG. 16 is similar to FIG. 14 except that the point of illumination by the light beam 1611 on the glass 1601 and the lens 1602 has moved. Thus, by moving the point of illumination there is provided moved beams 1609 and 1608 and a curvature 1607 for a different portion of the lens.

Figure 17:
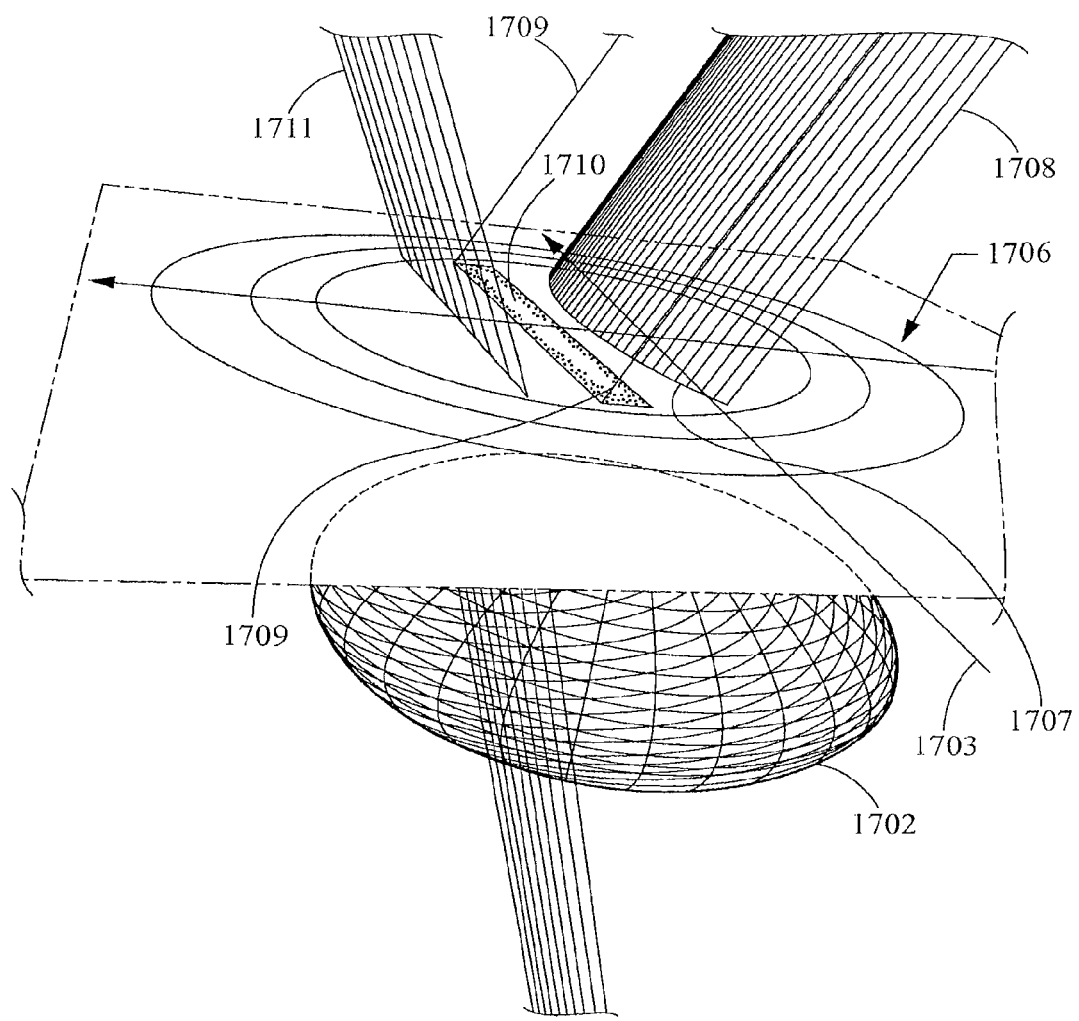

FIG. 17 is similar to FIGS. 15 and 14, except that as with FIG. 16 the point of illumination of light beam 1711 has been moved.

Figure 18:
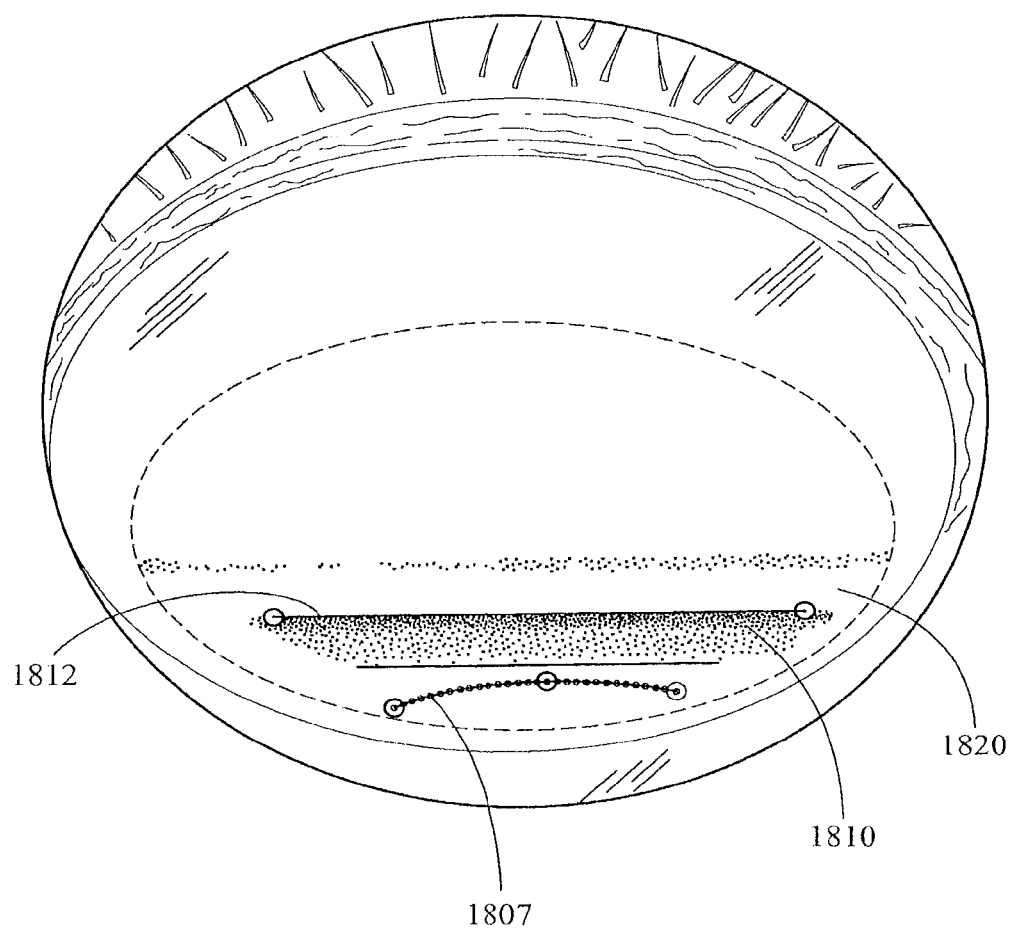

FIG. 18 is an image of the applanated cornea 1810 with the bottom surface of the glass plate 1820 being determined and labeled as line 1812. There is then provided a curvature of the lens 1807 for that particular portion of the lens that is being illuminated by the slit lamp. The determination of this curvature of the lens is based upon the application of a Random Sample Consensus ("RANSAC") algorithm to estimate with great certainty the parameters of a mathematical model from for the shape and position of the lens and in particular the lens capsule from a set of observed data, line beams such as for example 1408, 1508, 1608 & 1708. The monochrome camera images comprise an array of pixels representing light from the slit laser scattered from structures within the lens and cornea. The magnitude or brightness associated with each pixel in the image represents the amount of light scattered from a particular XYZ position within in the eye along the slit path. A highly scattering structure, such as the anterior lens capsule generates a bright arc of pixels in the image. However, viewed more closely, the image of the arc is granular and somewhat indistinct, containing some pixels which are bright and which should be definitely included in the determination of the curvature of the arc and some pixels which are of intermediate brightness which might or might not be included in the determination of the curvature. The estimation of the lens curvature involves selecting which pixels to include in the determination of curvature and then to estimate the curvature based on the selected pixels. These estimation can be done in two manners. In one manner the RANSAC algorithm is applied to all of the data obtained from the numerous camera images of slit lamp illuminations made at different slit positions and used simultaneously to determine a spherical shape. In another manner, which is presently preferred the RANSAC algorithm is applied to data from individual camera images of particular slit lamp positions and used to determine the shape and position of a circle from that each image. The circles, which were determined by RANSAC, are are used to estimate the parameters of the best fit sphere representing the lens shape, using a least squares non-liner regression. The RANSAC algorithm was first published by Fischler and Bolles in 1981.

In general the RANSAC algorithm as employed herein is based upon a number of algorithm parameters that are chosen to keep the level of probability of convergence of the fit to the circle fit parameters reasonably high. The approach is iterative wherein each iteration is used to refine the selection of which pixels (inliers) are best used to determine the parameters of the fit circle and which should be excluded (outliers) and to, at the same time refine the best fit parameters based on the pixels selected in the latest iteration. Thus, a model was fitted to the initial hypothetical inliers, to make an initial estimate of the parameters of the fit circle, i.e. shape and position of the lens from observed data. Based on the initial parameter estimates, all other data points, pixels, are checked to see how far they fall from the fitted model and the set of inliers and outliers is adjusted. The model was then re-estimated from all adjusted inliers. The model is evaluated by estimating a parameter related to the total magnitude of error of the inliers relative to the model. This procedure was repeated, and the precision of the estimate is refined at each iteration An example of a RANSAC algorithm is as follows:

```
input:
    data - a set of observed data points
    model - a model that can be fitted to data points
    n - the minimum number of data values required to fit the model
    k - the maximum number of iterations allowed in the algorithm
    t - a threshold value for determining when a data point fits a model
    d - the number of close data values required to assert that a model fits
        well to data
output: best_model - model parameters which best fit the data (or nil if
                no good model is found)
        best_consensus_set - data point from which this model has been
        estimated
        best_error - the error of this model relative to the data points
iterations := 0
best_model := nil
best_consensus_set := nil
best_error := infinity
while iterations < k
    maybe_inliers := n randomly selected values from data
    maybe_model := model parameters fitted to maybe_inliers
    consensus_set := maybe_inliers
    for every point in data not in maybe_inliers
        if point fits maybe_model with an error smaller than t
            add point to consensus_set
    if the number of elements in consensus_set is > d
    if the number of elements in consensus_set is > d
        better_model := model parameters fitted to all points in
        consensus_set
        this_error := a measure of how well better_model fits these
        points if this_err < best_err
            best_model := better_model
            best_consensus_set := consensus_set
            best_error := this_error
    increment iterations
return best_model, best_consensus_set, best_error
```

The series of best fit parameters for circles estimated for different slit beam locations is then used in a least squares algorithm to determine the radius of curvature and center of curvature of the anterior capsule, assuming that a sphere is a good representation of the shape of the capsule in the central region of interest.

Thus, by photographing the light scattered by lens structures from a laser slit beam positioned sequentially to a series of different slit locations and applying a RANSAC algorithm and/or a RANSAC algorithm and a least squares non-liner regression with a sphere fit, to the data obtained from each of those series of illuminations, a detained image of the shape and position of the lens relative to the laser device can be obtained. In the current embodiment, the shape and position of the anterior lens capsule is characterized by the estimation of the radius and center of curvature. Using this information, the position of the apex of the lens relative to the laser device, and in particular the therapeutic laser, can be determined for use in positioning and orienting the capsulotomy. Though not shown here, an exactly analogous method as described above for the anterior lens capsule can be used to determine the center and radius curvature of the anterior cornea. Since the center of curvature of the lens and cornea are known in most cases to fall close to the visual axis of the eye, these two points define a line which intersects the anterior lens capsule at or near the visual axis and position of the intersection can be used to center the capsulotomy cut at or near the visual axis as is generally desired for best optical outcome.

Figure 8A:
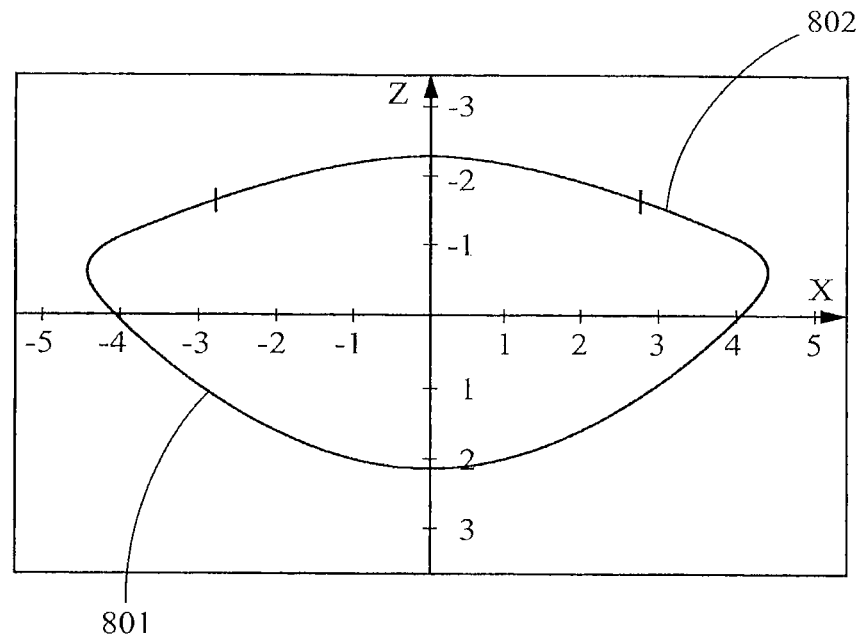
FIGS. 8A-D are diagrams illustrating a band cut circular capsulotomy.
Figure 8B:
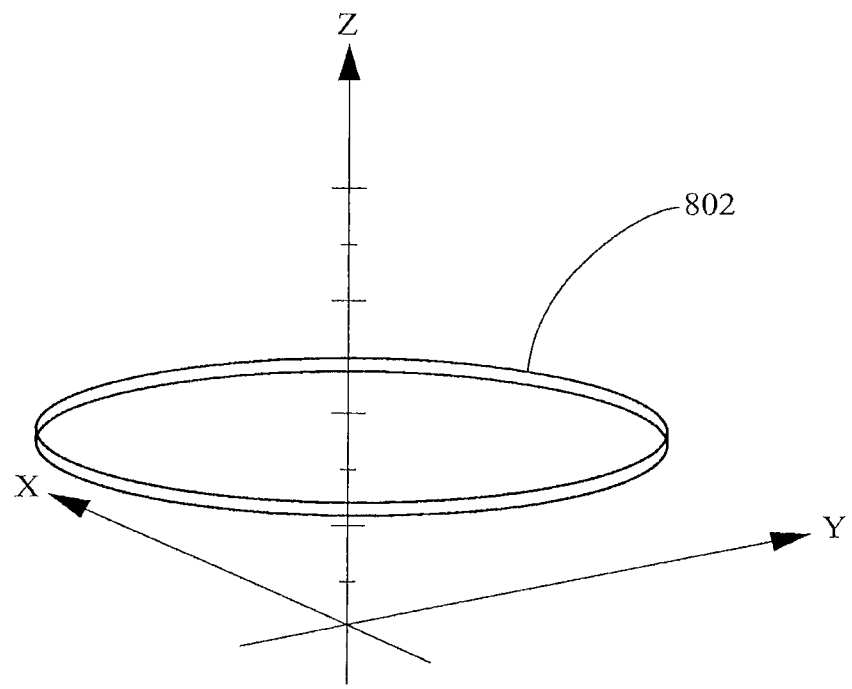
Figure 8C:
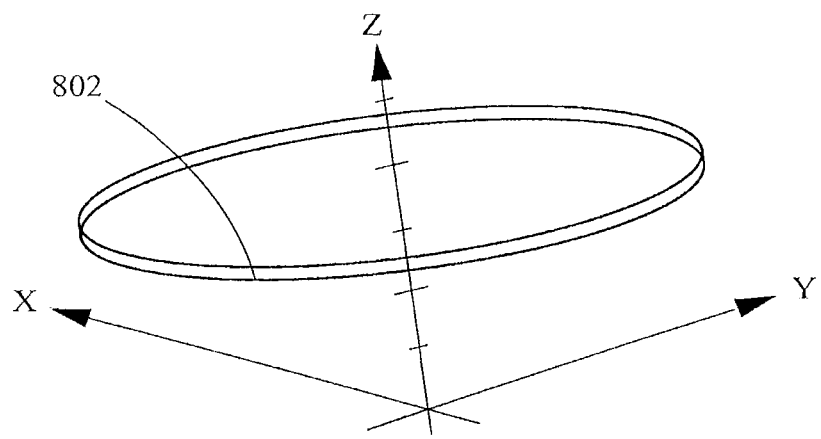
Figure 8D:
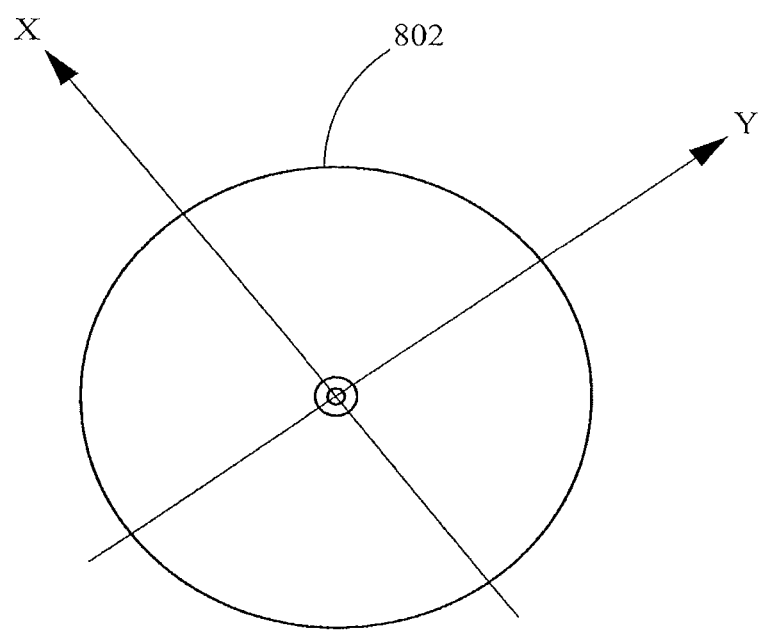

Having both the shape, position and apex of the lens provides the ability to greatly increase the accuracy and reproducibility of the capsulotomy. Determining the apex and shape of the lens relative to the laser device enables the use of a shot pattern for the capsulotomy that minimizes the number of shots that must be anterior to the anterior lens capsule to make certain that the capsulotomy is completed and the capsule portion can be readily removed. Thus, referring for example to FIG. 8A-C, the height of the ring pattern cut 802, i.e., the Z direction size, above the capsule 801 can be reduced, which may have benefits in reducing the formation of bubble in the aqueous.

A further optimization of the method and system to enhance flexibility regarding the aspiration of lens material from the lens capsule is provided. In sectioning the lens material it is possible that the some of the cut fragments of the fibrous mass may escape the capsular bag, either by floating or because of gas bubbles or just naturally, unless means of preventing such escape are provided. Therefore another aspect of the present method and system is to provide a means to restrain these fragments until they are ready to be aspirated out. Such a means is provided by performing only a partial cut of the capsule, leaving the capsule flap attached to serve as a restraint preventing and/or reducing the escape of sectioned lens material. Once aspiration is called for the partial cut to the capsule can be completed, i.e., the capsulotomy is completed, and the section lens material aspirated out of the lens capsule.

In all of the laser shot patterns provided herein it is preferred that the laser shot patterns generally follow the shape of the lens and placement of individual shots with respect to adjacent shots in the pattern are sufficiently close enough to each other, such that when the pattern is complete a sufficiently continuous layer and/or line and/or volume of lens material has been removed. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. For example, by way of illustration, for a 5 µm size spot with an energy sufficient to cause photodisruption, a spacing of 20 µm or greater results in individual gas bubbles, which are not coalesced and dissipate more quickly, than with close shot spaces with the same energy, which result in gas bubble coalescence. As the shot spacing gets closer together volume efficiency increases. As shot spacing gets closer together bubble coalescence also increases. Further, there comes a point where the shot spacing becomes so close that volume efficiency dramatically decreases. For example, by way of illustration, for a 450 femtosecond pulse width and 2 microjoules energy and about a 5 µm spot size with a 10 µm separation results in cleaving of transparent ocular tissue. As used herein, the term cleaving means to substantially separate the tissue. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics referrers to the effects that take place surrounding photodisruption, such as plasma formation and expansion, shock waive propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 5 KHz to 1 MHz., which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption.

The terms first, second, third, etc. as used herein are relative terms and must be viewed in the context in which they are used. They do not relate to timing, unless specifically referred to as such. Thus, a first cut may be made after a second cut. In general, it is preferred to fire laser shots in general from posterior points in the laser pattern to anterior points, to avoid and/or minimize the effect of the gas bubbles resulting from prior laser shots. However, because of the varied laser shot patterns that are provided herein, it is not a requirement that a strict posterior to anterior shot sequence be followed. Moreover, in the case of cataracts it may be advantageous to shoot from anterior to posterior, because of the inability of the laser to penetrate substantially beyond the cataract.

Thus, there is provided a method for the structural modification of the lens material to make it easier to remove while potentially increasing the safety of the procedure by reducing and/or eliminating the need to use high frequency ultrasonic energy used in Phaco emulsification. In general, the use of photodisruption cutting in a specific shape patterns is utilized to create sectioned lens material, i.e., to carve up the lens material into sectioned volumetric shapes, such as the tiny cube like structures shown in FIG. 7, which are small enough to be aspirated away with 1 to 2 mm sized aspiration needles.

Figure 7:
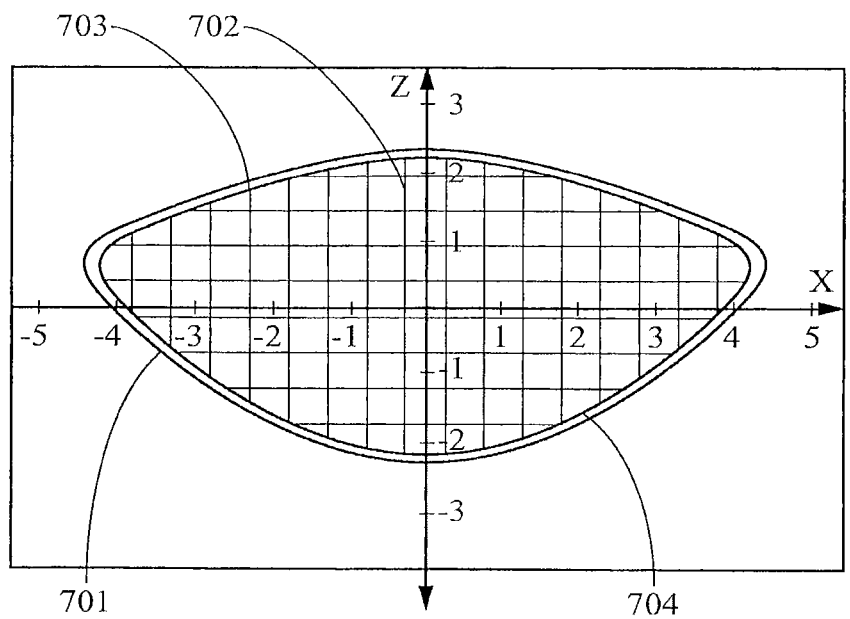
FIG. 7 is a diagram showing a shot pattern for the sectioning and removal of lens material.

As illustrated in FIG. 7, there is provided a shot pattern to create 0.5 mm sized cubes out of the lens material. Thus, there is provided an outer lens surface 701, which is formed by the lens capsule and thus an outer shape of the lens. There is further provided a shot pattern 702 that creates grid like cuts, the end of which cuts 703 essentially follows the shape of the lens. There may be further provided one shell cut 704, which is integral with the grid like cuts. The sequence of laser shots in the pattern in FIG. 7 may be executed from posterior to anterior, as in most of the patterns disclosed herein, to obtain more predictable results by reducing the variation caused by shooting through gas bubbles. However, it may be desirable to shoot cataracts from the anterior to the posterior for the purpose of choosing the lesser of two undesirable effects. Thus, it may be advantageous to shoot through the gas bubbles, or let them dissipate, rather then shooting through cataractus tissue, which much more severely scatters the light and more quickly prevents photodisruption compared to gas bubble interference. Accordingly, it is proposed to photodisrupt the most anterior sections of the cataract first, then move posteriorly, shooting through gas bubble remnants of cataractous tissue, to the next layer of cataract tissue below. In addition to shooting the laser in anterior z planes then moving posterior, it is further provided to essentially drill down anterior to posterior, which we call the z axis throughout this document and then move in x/y and drill down again. The shot pattern of FIG. 7 may also be applied to a clear lens and that lens material is subsequently removed. It is desirable when dealing with a clear lens that shooting from posterior to anterior is utilized.

The creation of capsulotomy for the surgeon to access the lens to remove the lens material is illustrated in FIGS. 8A-D. In these figures there is provided an outer surface 801, which surface is formed by the lens capsule, and thus an outer shape of the lens. There is further provided a ring shaped band cut 802 and shot pattern. This shot pattern is provided by placing the laser beam in a series of tightly placed shots around the ring and then continuing that sequence as the depth of the ring is increased. Thus, in general the shot will be distributed entirely around the ring at a particular depth before moving to a deeper depth. Thus, the figure shows the cross section view of this ring shaped annular band and accordingly provides for two sides 802 of the ring. The ring shaped capsulotomy cuts of 100 μm deep, approximately centered on the apex as determined by the above referenced method of the anterior lens capsule surface and precisely 5 mm in diameter. The diameter of the capsulotomy can be varied between about 0.1 mm to about 9 mm diameter.

Since the lens capsule is approximately 5 to 15 μm thick, it is desirable for the depth of the cut to be typically between 5 and several hundred um, although there is not much penalty for cutting several millimeters. With greater precision regarding the location and shape of the lens and lens apex the thickness of the band and in particular the amount of the band that is above the lens capsule and in the aqueous can be reduced. The shape of the capsulotomy can be elliptical with the x axis different then the y axis or other shapes. Thus, the shape of the capsulotomy can be any shape that provides a benefit for a particular IOL, for example the shape of the capsulotomy can be circular or elliptical geometric shapes or can be, square, rectangular, or other non-geometric shapes. The shape will be based at least in part upon and be determined at least in part by, the aspects of IOLs and in particular accommodating IOLs and IOLs that reduce and/or eliminate the need for spectacles. A particular IOL, such as FDA approved IOLs discussed herein, may benefit from and/or may require a particular capsulotomy shape and opening smoothness.

Figure 9A:
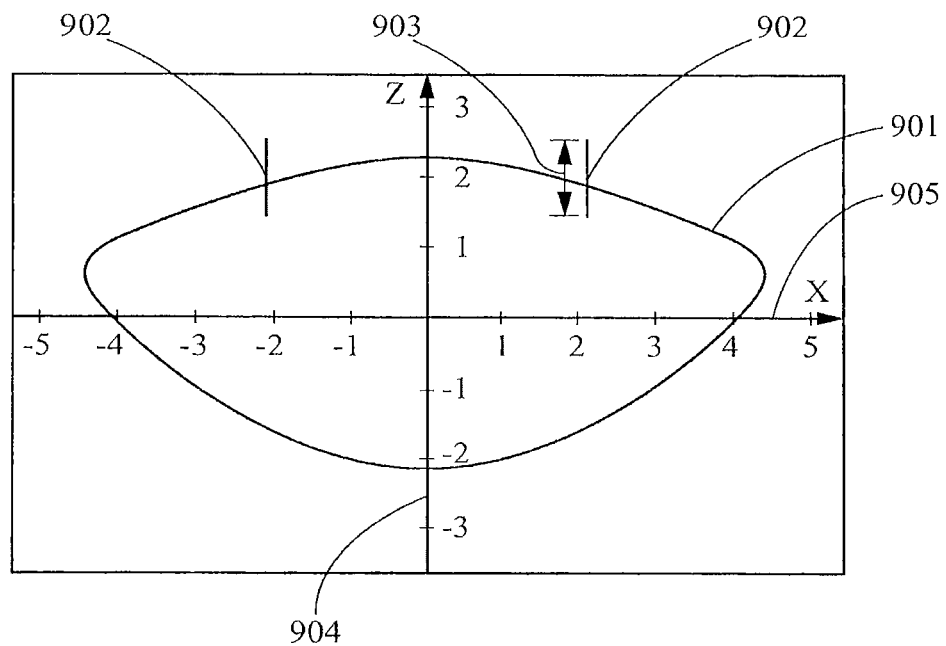
FIGS. 9A-C are diagrams illustrating a jigsaw cut circular shaped capsulotomy.
Figure 9B:
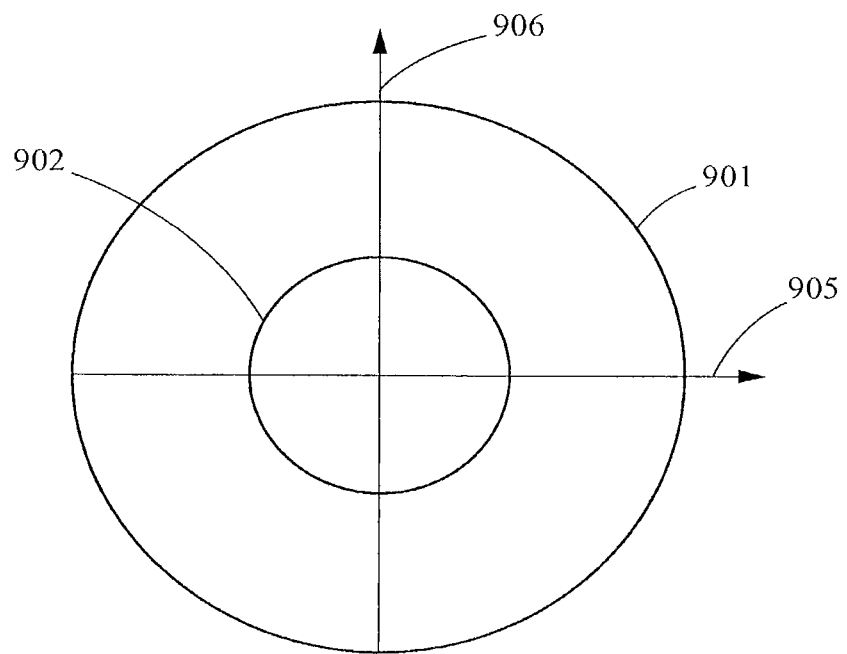
Figure 9C:
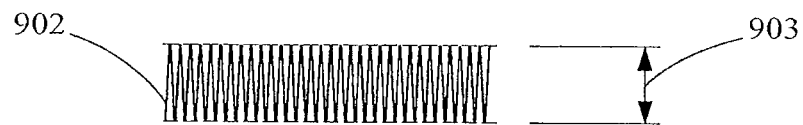

A jigsaw delivery sequence or pattern for performing a precision capsulotomy is further provided herein. As illustrated in FIGS. 9A-C, there is provided an outer surface 901, which surface is formed by the lens capsule, and thus an outer shape of the lens. FIG. 9A is a cross section of the lens with an X axis 905 and a Z axis 904. FIG. 9B is a top view of the lens down the Z axis and has X axis 905 and Y axis 906. There is further provided a jigsaw cut 902 and shot pattern, in the shape of a circle on the plane of the X axis 905 and the Y axis 906, when viewed down the Z axis 904. The laser shot pattern is delivered in a series of tightly spaced vertical sweeps over the same XY point of the pattern. Thus the Z position will change many times relative to the change in XY position as the shots are delivered. This rapidly changing Z position relative to the XY position is referred to as the vertical sweep of pattern 902 and the range of this sweep is shown by arrow 903. A particular IOL, such as FDA approved IOLs discussed herein, may benefit from and/or may require a particular capsulotomy shape and opening smoothness.

Figure 10A:
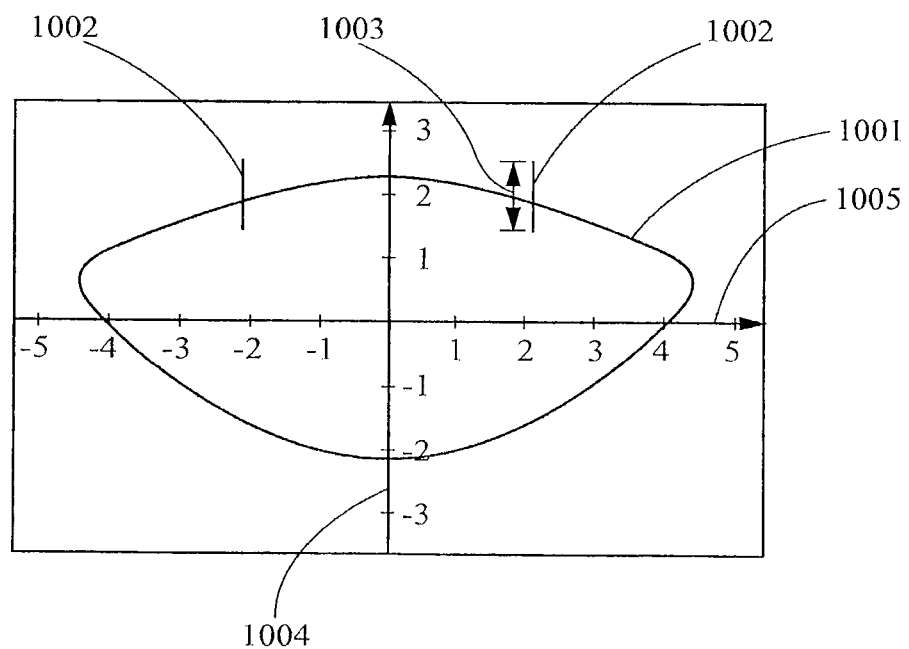
FIGS. 10A-C are diagrams illustrating a jigsaw cut elliptical shaped capsulotomy.
Figure 10B:
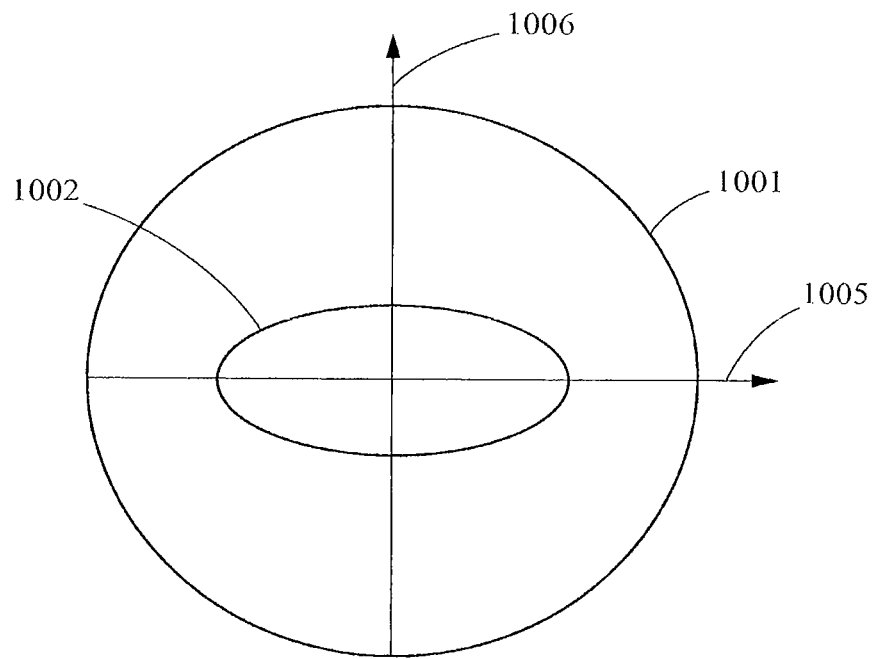
Figure 10C:
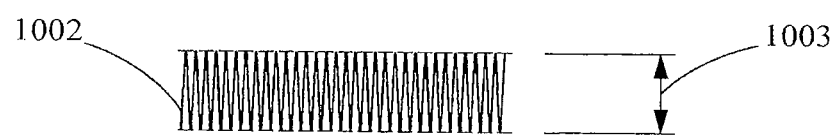

As illustrated in FIGS. 10A-C, there is provided an outer surface 1001, which surface is formed by the lens capsule, and thus an outer shape of the lens. FIG. 10A is a cross section of the lens with an X axis 1005 and a Z axis 1004. FIG. 10B is a top view of the lens down the Z axis and has X axis 1005 and Y axis 1006. There is further provided a jigsaw cut 1002 and shot pattern, in the shape of an ellipse on the plane of the X axis 1005 and the Y axis 1006, when viewed down the Z axis 1004. The laser shot pattern is delivered in a series of tightly spaced vertical sweeps over the same XY point of the pattern. Thus the Z position will change many times relative to the change in XY position as the shots are delivered. This rapidly changing Z position relative to the XY position is referred to as the vertical sweep of pattern 1002 and the range of this sweep is shown by arrow 1003. A particular IOL, such as FDA approved IOLs discussed herein, may benefit from and/or may require a particular capsulotomy shape and opening smoothness.

Figure 11A:
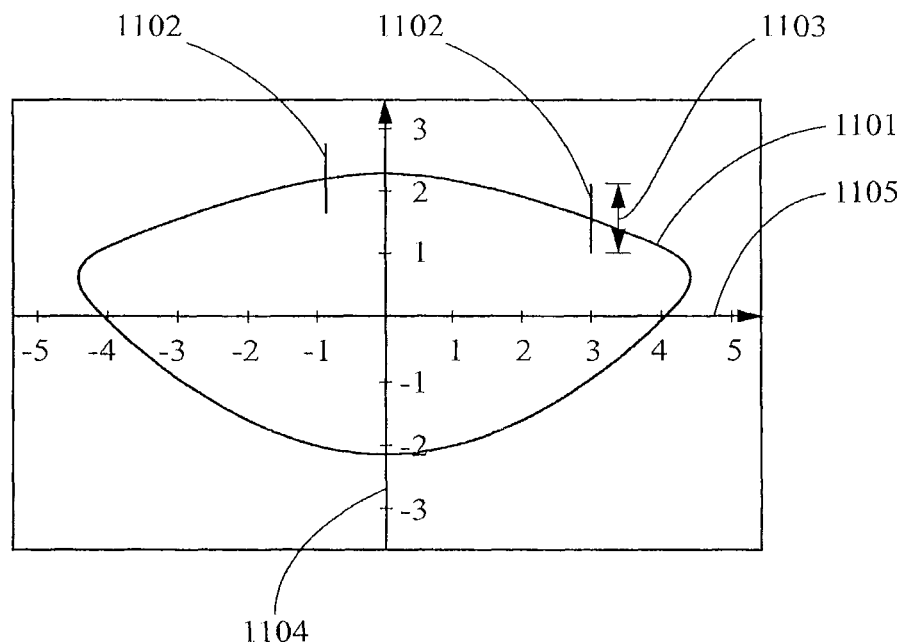
FIGS. 11A-C are diagrams illustrating a non-centered jigsaw cut circular shaped capsuolomy.
Figure 11B:
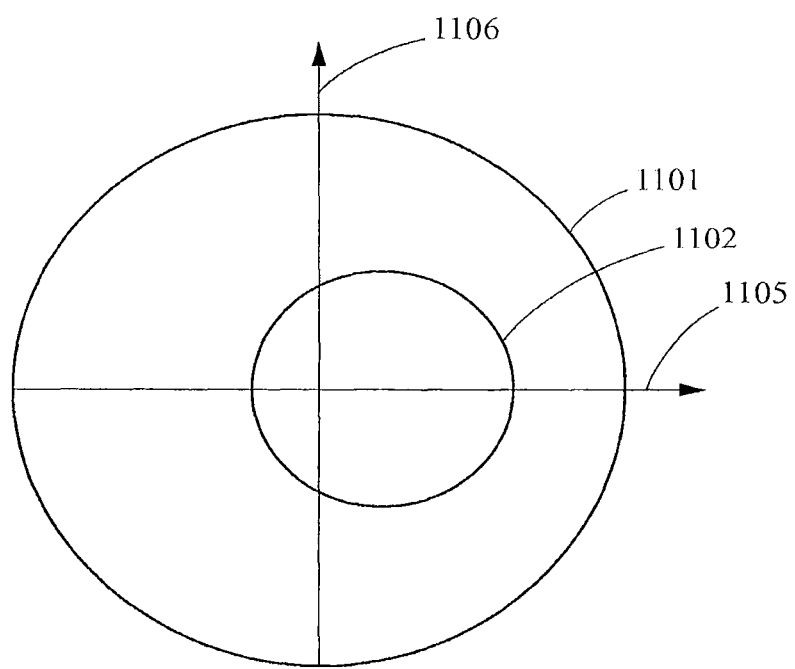
Figure 11C:
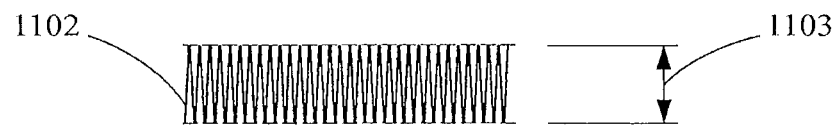

FIGS. 11A-C provide a circular shaped jigsaw cut of example 3 which has been placed off the center of the XY axis. Thus, there is provided an outer surface 1101, which surface is formed by the lens capsule, and thus an outer shape of the lens. There is provided an X axis 1105, a Y axis 1106 and a Z axis 1104. There is further provided a jigsaw cut 1102 and shot pattern, in the shape of a circle on the plane of the X axis 905 and the Y axis 906, when viewed down the Z axis 904. The center of the circle of this shot pattern 1102 is not centered upon the lens, i.e., the XY intersection, rather it is placed to right of center by about 1 mm.

Figure 12A:
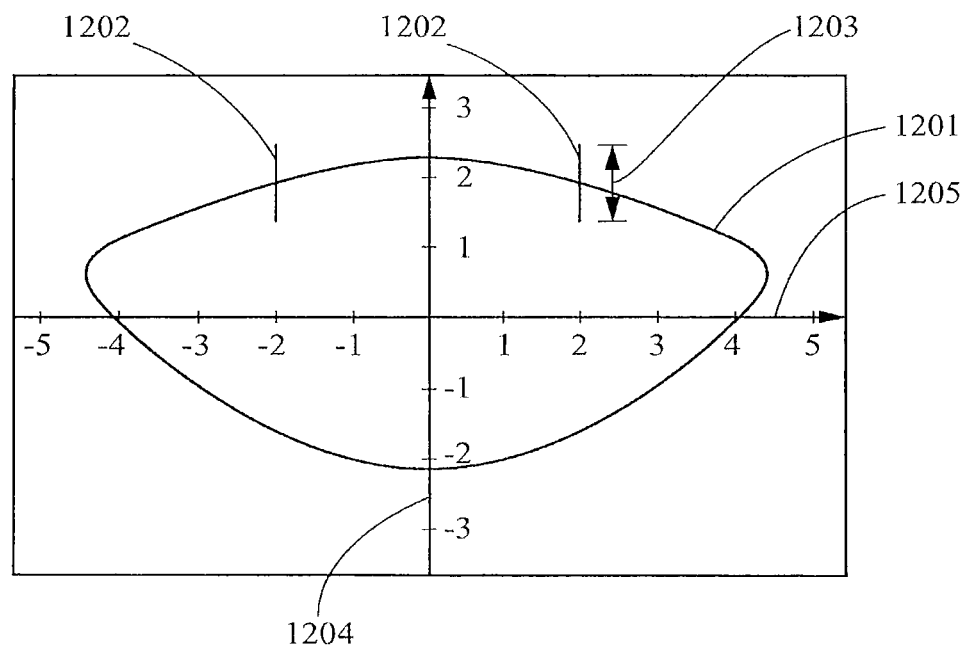
FIGS. 12A-C are diagrams illustrating a shot pattern having cuts and lands.
Figure 12B:
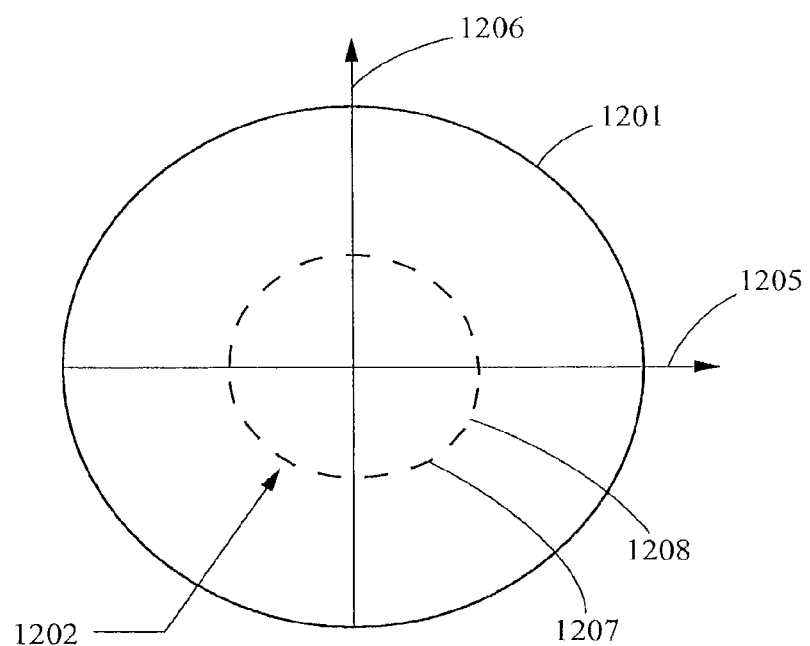
Figure 12C:
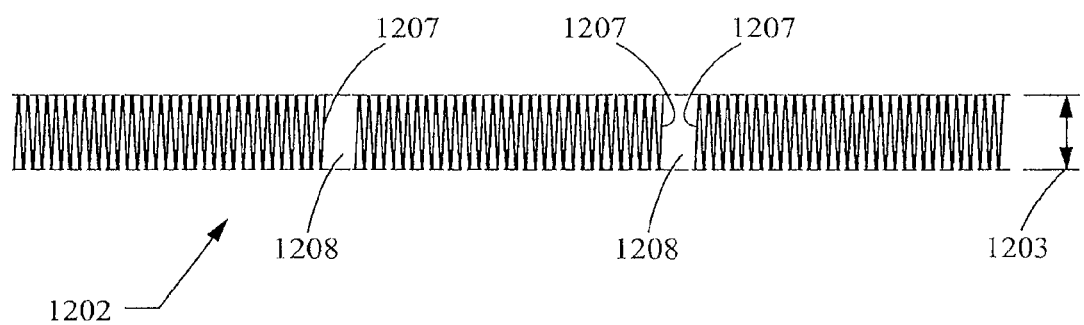

FIGS. 12A-C provide a circular cut and land jigsaw cut. Thus, there is provided an outer surface 1201, which surface is formed by the lens capsule, and thus an outer shape of the lens. There is provided an X axis 1205, a Y axis 1206 and a Z axis 1204. There is further provided a jigsaw cut 1202 and shot pattern, in the shape of a circle on the plane of the X axis 1205 and the Y axis 1206, when viewed down the Z axis 1204. The shot pattern 1202 has cuts 1207, i.e., lens material and in particular lens capsule material are removed, and lands 1208 where no material is removed.

The combination of the patterns and types of cuts provided herein can be interchanged and other shapes of patterns and position relative the XY center of the lens may be employed. Moreover, Because there is a greater likelihood for a missed laser shot with the band cut, i.e., the ring delivery sequence or pattern, such as shown in FIGS. 8A-D, than the jigsaw sequence, the use of the technique to determine the location, apex and shape of the lens is important, but not as critical, as when the ring sequence is being employed.

Figure 19:
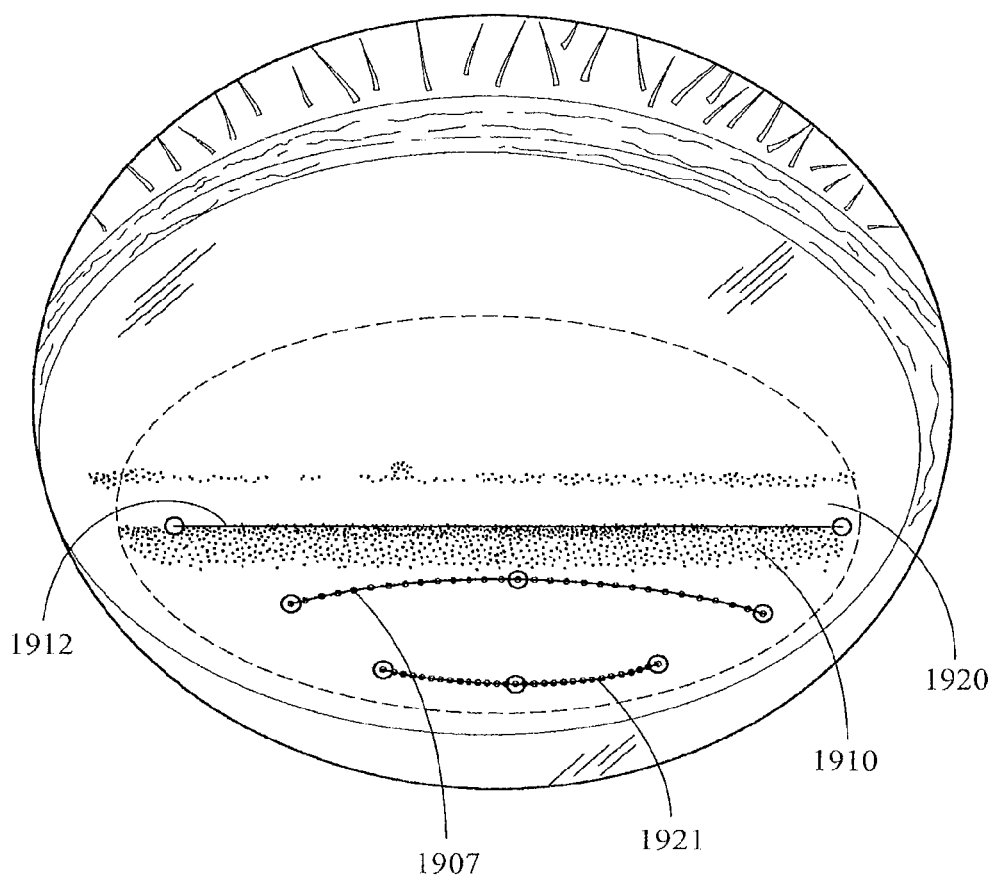

In FIG. 19 there is provided an image of a reference glass plate 1920, the posterior surface 1912 of the reference glass plate 1920 and the applanated cornea 1910. There is further provided the lens anterior capsule 1907 and the lens posterior capsule 1921.

Figure 20:
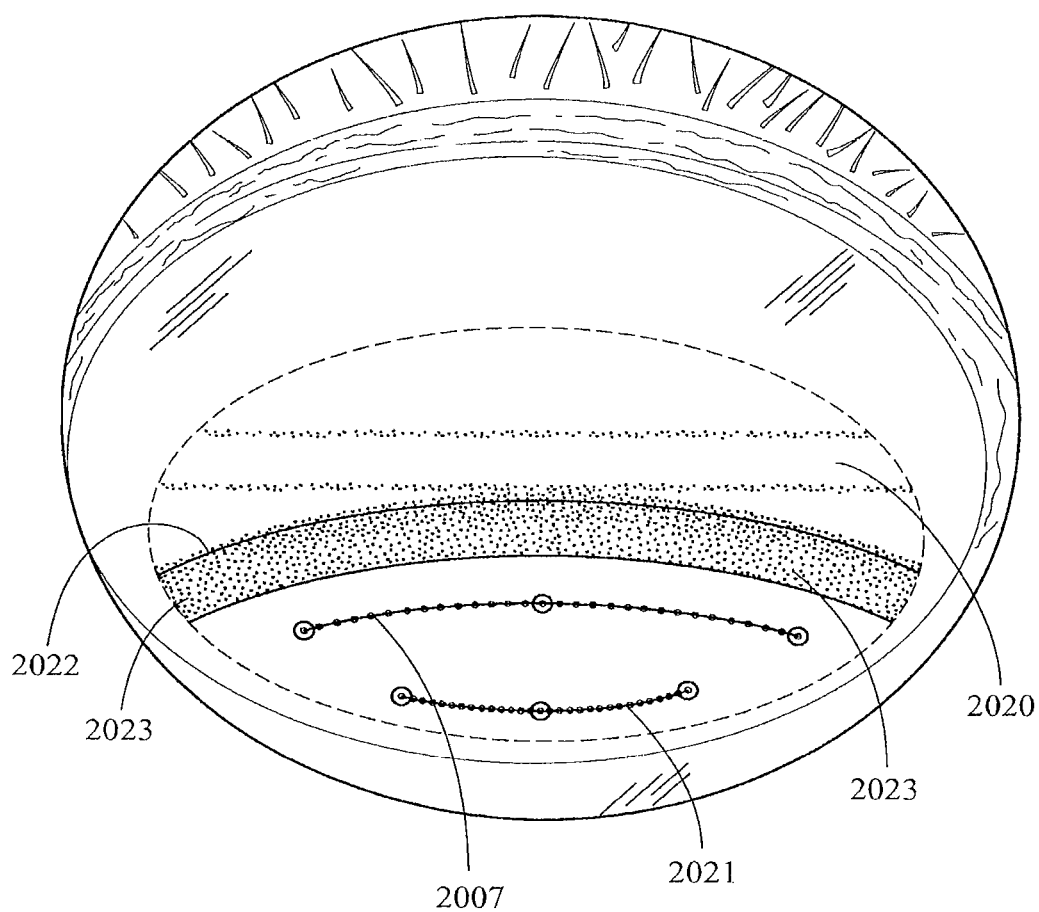

In FIG. 20 there is provided an image of a curved corneal interface 2022 and the un-applanated cornea 2023, as well as a reference glass 2020. There is further provided the lens anterior surface 2007 and the lens posterior surface 2021.

Thus, as show in FIGS. 19 and 20, by way of example, the present invention provides a novel means for determining the lens anterior and posterior capsule radii and centers of curvature.

From the foregoing description, one skilled in the art can readily ascertain the essential characteristics of this invention, and without departing from the spirit and scope thereof, can make various changes and/or modifications of the invention to adapt it to various usages and conditions.

What is claimed:

1. A system for providing accurate measurements of an eye, the system comprising:
    a light source that generates light;
    a glass plate positioned between said light source and an eye, wherein said light passes through said glass plate and enters into said eye and impinges on a lens of said eye;
    an imaging device that receives 1) a first set of light beams reflected from a bottom surface of said glass plate positioned nearest said eye and 2) a second set of light beams reflected from said lens and generates image information therefrom; and
    means for receiving said image information and processing said image information so that an image of said glass plate is generated and a measurement of said lens is generated.

2. The system of claim 1, wherein said light source comprises a slit lamp.

3. A system for providing accurate measurements of an eye, the system comprising:
    a light source that generates light;
    a glass plate positioned between said light source and an eye, wherein said light passes through said glass plate and enters into said eye and impinges on a lens of said eye, wherein said glass plate has a thickness of 1.57 mm and an index of refraction of 1.57;
    an imaging device that receives 1) a first set of light beams reflected from a bottom surface of said glass plate positioned nearest said eye and 2) a second set of light beams reflected from said lens and generates image information therefrom; and
    means for receiving said image information and processing said image information so that a measurement of said lens is generated.

4. A system for providing accurate measurements of an eye, the system comprising:
    a light source that generates light;
    a glass plate positioned between said light source and an eye, wherein said light passes through said glass plate and enters into said eye and impinges on a lens of said eye;
    an imaging device that receives 1) a first set of light beams reflected from a bottom surface of said glass plate positioned nearest said eye and 2) a second set of light beams reflected from said lens and generates image information therefrom; and
    means for receiving said image information and processing said image information so that a measurement of said lens is generated, wherein said light is directed through a theoretical planar surface and then passes through said glass plate; and wherein said light reflected from said lens intersects said planar surface along a curve that represents curvature of a portion of said lens from which said light is reflected from said lens.

5. The system of claim 4, wherein said means for receiving said image information and processing said image information determines an apex of said lens.

6. The system of claim 4, wherein said means for receiving said image information and processing said image information determines said curvature based upon application of a Random Sample Consensus algorithm to estimate with great certainty parameters of a mathematical model from for a shape and position of said lens.

7. The system of claim 6, wherein said image information comprises an array of pixels representing light from said lens and said curvature is determined by selecting which pixels to include in the determination of curvature and then to estimate the curvature based on said pixels selected.

8. A system for providing accurate measurements of an eye, the system comprising:
    a light source that generates light;
    a glass plate positioned between said light source and an eye, wherein said light passes through said glass plate and enters into said eye and impinges on a lens of said eye;
    an imaging device that receives 1) a first set of light beams reflected from a bottom surface of said glass plate positioned nearest said eye and 2) a second set of light beams reflected from said lens and generates image information therefrom; and
    means for receiving said image information and processing said image information so that a measurement of said lens is generated, wherein said bottom surface applanates a cornea of said eye.

9. The system of claim 8, wherein said light is directed through a theoretical planar surface and then passes through said glass plate; and wherein said light reflected from said lens intersects said planar surface along a curve that represents curvature of a portion of said lens from which said light is reflected from said lens.

10. The system of claim 8, wherein said means for receiving said image information and processing said image information determines an apex of said lens.

11. The system of claim 8, wherein said means for receiving said image information and processing said image information determines said curvature based upon application of a Random Sample Consensus algorithm to estimate with great certainty parameters of a mathematical model from for a shape and position of said lens.

12. The system of claim 11, wherein said image information comprises an array of pixels representing light from said lens and said curvature is determined by selecting which pixels to include in the determination of curvature and then to estimate the curvature based on said pixels selected.

13. A method for providing accurate measurements of an eye, the method comprising:
    generating light from a light source;
    positioning a glass plate between said light source and an eye, wherein said light passes through said glass plate and enters into said eye and impinges on a lens of said eye;
    generating image information from 1) a first set of light beams reflected from a bottom surface of said glass plate positioned nearest said eye and 2) a second set of light beams reflected from said lens and generates image information; and
    processing said image information so that an image of said glass plate is generated and a measurement of said lens is generated.

14. The method of claim 13, wherein said light source comprises a slit lamp.

15. A method for providing accurate measurements of an eye, the system comprising:
    generating light from a light source;
    positioning a glass plate between said light source and an eye, wherein said glass plate has a thickness of 1.57 mm and an index of refraction of 1.57, and wherein said light passes through said glass plate and enters into said eye and impinges on a lens of said eye;

generating image information from 1) a first set of light beams reflected from a bottom surface of said glass plate positioned nearest said eye and 2) a second set of light beams reflected from said lens and generates image information; and processing said image information so that a measurement of said lens is generated.

16. A method for providing accurate measurements of an eye, the system comprising:

generating light from a light source;

positioning a glass plate between said light source and an eye, wherein said light passes through said glass plate and enters into said eye and impinges on a lens of said eye;

generating image information from 1) a first set of light beams reflected from a bottom surface of said glass plate positioned nearest said eye and 2) a second set of light beams reflected from said lens and generates image information; and processing said image information so that a measurement of said lens is generated, wherein said light is directed through a theoretical planar surface and then passes through said glass plate; and wherein said light reflected from said lens intersects said planar surface along a curve that represents curvature of a portion of said lens from which said light is reflected from said lens.

17. The method of claim 16, wherein said processing comprises determining an apex of said lens.

18. The method of claim 16, wherein said processing comprises determining said curvature based upon application of a Random Sample Consensus algorithm to estimate with great certainty parameters of a mathematical model from for a shape and position of said lens.

19. The method of claim 18, wherein said image information comprises an array of pixels representing light from said lens and said curvature is determined by selecting which pixels to include in the determination of curvature and then to estimate the curvature based on said pixels selected.

20. A method for providing accurate measurements of an eye, the system comprising:

generating light from a light source;

positioning a glass plate between said light source and an eye, wherein said light passes through said glass plate and enters into said eye and impinges on a lens of said eye;

generating image information from 1) a first set of light beams reflected from a bottom surface of said glass plate positioned nearest said eye and 2) a second set of light beams reflected from said lens and generates image information; and processing said image information so that a measurement of said lens is generated, wherein said bottom surface applanates a cornea of said eye.

21. The method of claim 20, wherein said light is directed through a theoretical planar surface and then passes through said glass plate; and wherein said light reflected from said lens intersects said planar surface along a curve that represents curvature of a portion of said lens from which said light is reflected from said lens.

22. The method of claim 21, wherein said processing comprises determining an apex of said lens.

23. The method of claim 21, wherein said processing comprises determining said curvature based upon application of a Random Sample Consensus algorithm to estimate with great certainty parameters of a mathematical model from for a shape and position of said lens.

24. The method of claim 23, wherein said image information comprises an array of pixels representing light from said lens and said curvature is determined by selecting which pixels to include in the determination of curvature and then to estimate the curvature based on said pixels selected.

* * * * *